US011826951B2

United States Patent
Boyer et al.

(10) Patent No.: US 11,826,951 B2
(45) Date of Patent: Nov. 28, 2023

(54) TEMPERATURE-CONTROLLED MULTI-MATERIAL OVERPRINTING

(71) Applicant: Cellink AB, Gothenburg (SE)

(72) Inventors: Christen J. Boyer, Germantown, MD (US); Hector Martinez, Gothenburg (SE); Erik Gatenholm, Gothenburg (SE)

(73) Assignee: Cellink AB, Gothenburg (SE)

( * ) Notice: Subject to any disclaimer, the term of this patent is extended or adjusted under 35 U.S.C. 154(b) by 0 days.

(21) Appl. No.: 17/011,767

(22) Filed: Sep. 3, 2020

(65) Prior Publication Data

US 2021/0069964 A1    Mar. 11, 2021

Related U.S. Application Data

(60) Provisional application No. 62/897,188, filed on Sep. 6, 2019.

(51) Int. Cl.
*B29C 64/129* (2017.01)
*B29C 64/188* (2017.01)
(Continued)

(52) U.S. Cl.
CPC .......... *B29C 64/129* (2017.08); *B29C 64/188* (2017.08); *B29C 64/205* (2017.08);
(Continued)

(58) Field of Classification Search
CPC ................................................... B29C 64/188
See application file for complete search history.

(56) References Cited

U.S. PATENT DOCUMENTS

| 5,236,416 A | 8/1993 | McDaniel et al. |
| 6,103,790 A | 8/2000 | Cavaille et al. |

(Continued)

FOREIGN PATENT DOCUMENTS

| CN | 103893825 B | 6/2015 | |
| CN | 108248020 A | * 7/2018 | ............. B33Y 30/00 |

(Continued)

OTHER PUBLICATIONS (Abushall, Hany et al.) Co-Pending U.S. Appl. No. 17/434,321, filed Aug. 26, 2021, Specification, Claims, and Figures.
(Continued)

*Primary Examiner* — Timothy Kennedy
(74) *Attorney, Agent, or Firm* — New River Valley IP Law, P.C.; Michele L. Mayberry

(57) ABSTRACT

A three-dimensional (3D) bioprinting method and system are disclosed. The method includes disposing/immersing a printing platform or surface into a first bioink, such as a bioink resin, curing one or more layer of the first bioink resin onto the printing platform or surface, and removing the printing platform or surface from the first bioink resin. The process is repeated with a second bioink resin such that the second bioink resin is cured on top of the one or more layer of first bioink resin, and can be further repeated with a third or even fourth bioink resin. By varying constituents of one or more or each bioink resin (such as living cell type or polymer), complex, multilayered tissues can be engineered. A system capable of performing the method is also disclosed.

15 Claims, 7 Drawing Sheets

(51) Int. Cl.

| | |
|---|---|
| *B29C 64/241* | (2017.01) |
| *B29C 64/236* | (2017.01) |
| *B29C 64/232* | (2017.01) |
| *B29C 64/264* | (2017.01) |
| *B29C 64/205* | (2017.01) |
| *B29C 64/255* | (2017.01) |
| *B29C 64/245* | (2017.01) |
| B29K 105/12 | (2006.01) |
| B33Y 10/00 | (2015.01) |
| B33Y 30/00 | (2015.01) |
| B33Y 40/20 | (2020.01) |
| B33Y 70/00 | (2020.01) |
| B29K 105/00 | (2006.01) |

(52) U.S. Cl.
CPC .......... *B29C 64/232* (2017.08); *B29C 64/236* (2017.08); *B29C 64/241* (2017.08); *B29C 64/245* (2017.08); *B29C 64/255* (2017.08); *B29C 64/264* (2017.08); B29K 2105/0035 (2013.01); B29K 2105/124 (2013.01); B33Y 10/00 (2014.12); B33Y 30/00 (2014.12); B33Y 40/20 (2020.01); B33Y 70/00 (2014.12)

(56) References Cited

U.S. PATENT DOCUMENTS

| | | | |
|---|---|---|---|
| 6,509,733 | B2 | 1/2003 | Blubaugh et al. |
| 6,942,830 | B2 | 9/2005 | Mülhaupt et al. |
| 7,052,263 | B2 | 5/2006 | John |
| 7,105,357 | B1 | 9/2006 | Kalkum et al. |
| 7,122,712 | B2 | 10/2006 | Lutri et al. |
| 7,195,472 | B2 | 3/2007 | John |
| 7,636,610 | B2 | 12/2009 | Schillen et al. |
| 7,783,371 | B2 | 8/2010 | John et al. |
| 7,892,474 | B2 | 2/2011 | Shkolnik et al. |
| 7,894,921 | B2 | 2/2011 | John et al. |
| RE43,955 | E | 2/2013 | Shkolnik et al. |
| 8,394,313 | B2 | 3/2013 | El-Siblani et al. |
| 8,691,974 | B2 | 4/2014 | Gatenholm et al. |
| 8,931,880 | B2 | 1/2015 | Murphy et al. |
| 9,073,261 | B2 | 7/2015 | El-Siblani et al. |
| 9,315,043 | B2 | 4/2016 | Murphy et al. |
| 9,662,821 | B2 | 5/2017 | Clineff et al. |
| 9,725,613 | B2 | 8/2017 | García et al. |
| 10,226,894 | B2 | 3/2019 | Houben et al. |
| 10,272,664 | B2 | 4/2019 | Hays et al. |
| 10,675,379 | B2 | 6/2020 | Gatenholm |
| 11,186,736 | B2 | 11/2021 | Martinez et al. |
| 2003/0059708 | A1* | 3/2003 | Yamamura ............. B33Y 70/00 430/269 |
| 2005/0056713 | A1 | 3/2005 | Tisone et al. |
| 2008/0305012 | A1 | 12/2008 | Camenisch |
| 2009/0003696 | A1 | 1/2009 | Ishii et al. |
| 2009/0022791 | A1 | 1/2009 | Obae et al. |
| 2010/0175759 | A1 | 7/2010 | Ikushima |
| 2010/0200752 | A1 | 8/2010 | Lee et al. |
| 2010/0206224 | A1 | 8/2010 | Thurner et al. |
| 2011/0024699 | A1 | 2/2011 | Lin et al. |
| 2011/0151482 | A1 | 6/2011 | Emery et al. |
| 2013/0309295 | A1 | 11/2013 | Gatenholm |
| 2014/0074274 | A1 | 3/2014 | Douglas et al. |
| 2015/0013476 | A1 | 1/2015 | Telimaa et al. |
| 2015/0045928 | A1 | 2/2015 | Perez et al. |
| 2015/0050719 | A1 | 2/2015 | Bammesberger et al. |
| 2015/0072293 | A1 | 3/2015 | DeSimone et al. |
| 2015/0102351 | A1 | 4/2015 | Kimura |
| 2015/0105891 | A1 | 4/2015 | Golway et al. |
| 2015/0246482 | A1 | 9/2015 | El-Siblani et al. |
| 2015/0290874 | A1* | 10/2015 | Chen .................... B29C 64/129 425/174.4 |
| 2015/0375453 | A1 | 12/2015 | Yost et al. |
| 2016/0236414 | A1 | 8/2016 | Reese et al. |
| 2016/0243618 | A1 | 8/2016 | Heugel et al. |
| 2016/0271870 | A1* | 9/2016 | Brown, Jr. ............ B29C 64/153 |
| 2016/0271875 | A1* | 9/2016 | Brown, Jr. ............ B29C 64/135 |
| 2016/0288414 | A1 | 10/2016 | Ozbolat et al. |
| 2017/0031149 | A1 | 2/2017 | Levin et al. |
| 2017/0079262 | A1 | 3/2017 | Rowley et al. |
| 2017/0080641 | A1 | 3/2017 | El-Siblani |
| 2017/0100899 | A1 | 4/2017 | El-Siblani et al. |
| 2017/0172765 | A1 | 6/2017 | Solorzano et al. |
| 2017/0199507 | A1 | 7/2017 | Murphy et al. |
| 2017/0210077 | A1* | 7/2017 | Ermoshkin ........... B29C 64/124 |
| 2017/0216498 | A1 | 8/2017 | Kang et al. |
| 2017/0225393 | A1 | 8/2017 | Shkolnik |
| 2017/0348458 | A1 | 12/2017 | Kesti et al. |
| 2017/0368225 | A1 | 12/2017 | Gatenholm |
| 2018/0071740 | A1 | 3/2018 | Brueckner et al. |
| 2018/0273904 | A1 | 9/2018 | Skardal |
| 2018/0281280 | A1 | 10/2018 | Solorzano et al. |
| 2018/0297270 | A1 | 10/2018 | Liu et al. |
| 2018/0326665 | A1 | 11/2018 | Gatenholm et al. |
| 2018/0326666 | A1 | 11/2018 | Kelly et al. |
| 2018/0341248 | A1 | 11/2018 | Mehr et al. |
| 2018/0345563 | A1 | 12/2018 | Sternå et al. |
| 2018/0348247 | A1 | 12/2018 | Ando |
| 2018/0370116 | A1 | 12/2018 | Huang et al. |
| 2019/0016052 | A1 | 1/2019 | Clark |
| 2019/0160203 | A1 | 5/2019 | Gatenholm |
| 2019/0209738 | A1 | 7/2019 | Gatenholm |
| 2019/0344500 | A1 | 11/2019 | Côté |
| 2020/0070421 | A1 | 3/2020 | Horn et al. |
| 2020/0071550 | A1 | 3/2020 | Gaharwar et al. |
| 2020/0122135 | A1 | 4/2020 | Abate et al. |
| 2020/0139623 | A1 | 5/2020 | Kalpio et al. |
| 2020/0164103 | A1 | 5/2020 | Gatenholm |
| 2020/0206385 | A1 | 7/2020 | Gatenholm |
| 2021/0001009 | A1 | 1/2021 | Redwan et al. |
| 2021/0031456 | A1 | 2/2021 | Thayer et al. |
| 2021/0179871 | A1 | 6/2021 | Martinez et al. |
| 2022/0105676 | A1 | 4/2022 | Boyer et al. |
| 2022/0161499 | A1 | 5/2022 | Abushall et al. |

FOREIGN PATENT DOCUMENTS

| | | |
|---|---|---|
| CN | 108248020 A | 7/2018 |
| CN | 111618302 A | 9/2020 |
| DE | 202015000178 U1 | 4/2015 |
| EP | 2199380 A2 | 6/2010 |
| EP | 1732746 B1 | 4/2011 |
| EP | 2808671 A1 | 12/2014 |
| EP | 2633032 B1 | 2/2015 |
| EP | 2916158 A1 | 9/2015 |
| EP | 2975115 A1 | 1/2016 |
| EP | 3366458 A1 | 8/2018 |
| EP | 3415300 A1 | 12/2018 |
| EP | 3463822 A1 | 4/2019 |
| EP | 3469004 A4 | 5/2020 |
| EP | 3799571 A1 | 4/2021 |
| EP | 3931532 A1 | 1/2022 |
| FI | 123988 B | 1/2014 |
| HR | PK20140564 A2 | 12/2015 |
| HR | PK20140564 B | 5/2017 |
| JP | 2000513258 A | 10/2000 |
| JP | 2005003610 A | 1/2005 |
| JP | 2010533855 A | 10/2010 |
| JP | 2013181167 A | 9/2013 |
| JP | 2013541956 A | 11/2013 |
| JP | 2018501845 A | 1/2018 |
| JP | 7053503 B2 | 4/2022 |
| JP | 7312761 B2 | 7/2023 |
| KR | 101502236 B1 | 3/2015 |
| WO | 2004092672 A2 | 10/2004 |
| WO | 2008055533 A1 | 5/2008 |
| WO | 2008122661 A1 | 10/2008 |
| WO | 2009053100 | 5/2010 |
| WO | 2012051718 A1 | 4/2012 |
| WO | 2012056109 A2 | 5/2012 |
| WO | 2012056111 A2 | 5/2012 |
| WO | 2012071578 A2 | 5/2012 |
| WO | 2012056110 A3 | 6/2012 |
| WO | 2012024675 A9 | 2/2013 |

(56) References Cited

FOREIGN PATENT DOCUMENTS

| WO | 2014049204 A1 | 4/2014 |
|---|---|---|
| WO | 2015066705 A1 | 5/2015 |
| WO | 2015101712 A1 | 7/2015 |
| WO | 2015164844 A1 | 10/2015 |
| WO | 2015175457 A1 | 11/2015 |
| WO | 2015148646 A3 | 1/2016 |
| WO | 2016073782 A1 | 5/2016 |
| WO | 2016091336 A1 | 6/2016 |
| WO | 2016092106 A1 | 6/2016 |
| WO | 2016100856 A1 | 6/2016 |
| WO | 2017040675 A1 | 3/2017 |
| WO | 2017109394 A1 | 6/2017 |
| WO | 2017109395 A1 | 6/2017 |
| WO | 2017115056 A1 | 7/2017 |
| WO | 2017152142 A1 | 9/2017 |
| WO | 2017184839 A1 | 10/2017 |
| WO | 2017210663 A1 | 12/2017 |
| WO | 2017214592 A1 | 12/2017 |
| WO | 2018119989 A1 | 7/2018 |
| WO | 2018169965 A1 | 9/2018 |
| WO | 2018187380 A1 | 10/2018 |
| WO | 2018234837 A1 | 12/2018 |
| WO | 2019043529 A1 | 3/2019 |
| WO | 2019109127 A1 | 6/2019 |
| WO | 2019145795 A2 | 8/2019 |
| WO | 2019246623 A9 | 2/2020 |
| WO | 2020077118 A1 | 4/2020 |
| WO | 2020086941 A1 | 4/2020 |
| WO | 2020094913 A1 | 5/2020 |
| WO | 2020157077 A2 | 8/2020 |
| WO | 2020165322 A1 | 8/2020 |
| WO | 2020176079 A1 | 9/2020 |
| WO | 2021231717 A1 | 11/2021 |
| WO | 2021243046 A1 | 12/2021 |
| WO | 2022192768 A1 | 9/2022 |

OTHER PUBLICATIONS (Gatenholm, Erik et al.) Co-pending International Application No. PCT/EP2020/052062, filed Jan. 28, 2020, Specification, Claims, Figures, 49 pages (See WO2020157077).
(Martinez, Hector et al.) Co-pending International Application No. PCT/EP2020/053721, filed Feb. 13, 2020, Specification, Claims, Figures, 46 pages (See WO2020/165322).
(Redwan, Adel Itedale Namro et al.) Co-pending European Patent Application No. 19874873.3 filed Dec. 29, 2020, Specification and Figures (See PCT/US2019/058025) and amended claims (3 pages).
(Redwan, Adel Itedale Namro et al.) Co-pending Korean Application No. 10-2020-7031999 filed Nov. 5, 2020, Specification, Claims, and Figures (See PCT/2019/058025).
Apelgren, P. et al., PLoS ONE, "Chondrocytes and stem cells in 3D-bioprinted structures create human cartilage in vivo", published Dec. 13, 2017, vol. 12, No. 12, 16 pages.
Bodin, A. et al., "Modification of Nanocellulose with a Xyloglucan-RGD Conjugate Enhances Adhesion and Proliferation of Endothelial Cells: Implications for Tissue Engineering", Biomacromolecules 2007, 8, 3697-3704, 8 pages.
Chang, R. et al., "Direct Cell Writing of 3D Microorgan for In Vitro Pharmacokinetic Model", Tissue Engineering: Part C, vol. 14, No. 2, 2008, 11 pages.
Co-pending U.S. Appl. No. 15/537,154 Notice of Allowance dated Apr. 28, 2020, 6 pages.
Co-pending U.S. App. No. 15/537,154 Supplemental Notice of Allowance dated May 5, 2020, 3 pages.
Co-pending U.S. Appl. No. 16/306,436, Non-Final Office Action dated Nov. 18, 2021, 13 pages.
Co-pending U.S. Appl. No. 16/306,436, Response to Jun. 28 2021 Restriction Requirement, filed Aug. 27, 2021, 5 pages.
Co-pending U.S. Appl. No. 16/306,436, Restriction Requirement dated Jun. 28, 2021, 11 pages.
Co-Pending U.S. Appl. No. 16/979,452, Final Office Action dated Jul. 13, 2021, 18 pages.
Co-Pending U.S. Appl. No. 16/979,452, Non-Final Office Action dated Mar. 30, 2021, 16 pages.
Co-Pending U.S. Appl. No. 16/979,452, Response to Jul. 13, 2021 Final Office Action, filed Nov. 15, 2021, 8 pages.
Co-Pending U.S. Appl. No. 16/979,452, Response to Mar. 10, 2021 Restriction Requirement dated Mar. 17, 2021, 3 pages.
Co-Pending U.S. Appl. No. 16/979,452, Response to Mar. 30, 2021 Non-Final Office Action dated Jun. 24, 2021, 8 pages.
Co-Pending U.S. Appl. No. 16/979,452, Restriction Requirement dated Mar. 10, 2021, 11 pages.
Co-Pending U.S. Appl. No. 17/048,755, Non-Final Office Action dated Jun. 17, 2021, 11 pages.
Co-Pending U.S. Appl. No. 17/048,755, Notice of Allowance dated Aug. 11, 2021, 10 pages.
Co-Pending U.S. Appl. No. 17/048,755, Response to Jun. 17, 2021 Non-Final Office Action dated Jul. 2, 2021, 8 pages.
Co-Pending U.S. Appl. No. 17/048,755, Response to May 13, 2021 Restriction Requirement, filed May 20, 2021, 2 pages.
Co-Pending U.S. Appl. No. 17/048,755, Restriction Requirement, dated May 13, 2021, 7 pages.
Co-Pending U.S. Appl. No. 17/434,321, Preliminary Amendment filed Aug. 26, 2021, 7 pages.
Co-pending European Application No. 17807642.8, Response to Jul. 3, 2020 Communication pursuant to Rules 70(2) and 70a(2) EPC filed Jan. 13, 2021, 12 pages.
Co-pending European Patent Application No. 17811137.3, Communication under Article 94(3) EPC dated Dec. 10, 2020, 6 pages.
Co-pending European Patent Application No. 17811137.3, Response to Apr. 1, 2020 Communication pursuant to Rules 70(2) and 70a(2) EPC filed Oct. 30, 2020, 11 pages.
Co-pending European Patent Application No. 17811137.3, Response to Dec. 10, 2020 Communication under Article 94(3) EPC, filed Jun. 21, 2021, 15 pages.
Co-pending International Application No. PCT/EP2020/052062, International Search Report and Written Opinion, dated Aug. 24, 2020, 19 pages.
Co-pending International Application No. PCT/EP2020/053721, International Search Report and Written Opinion, dated May 18, 2020, 11 pages.
Co-pending Japanese Application No. 2018-564332, Office Action dated May 14, 2021, 9 pages and English Translation, 10 pages.
Co-pending Japanese Application No. 2018-564332, Response to May 14, 2021 Office Action filed Oct. 13, 2021, 6 pages and English Translation of Amended Claims, 5 pages.
Co-pending Japanese Application No. 2019-516082, First Office Action dated Mar. 1, 2021 (3 pages) and English Translation (4 pages).
Co-pending Japanese Application No. 2019-516082, Response to First Office Action filed Aug. 2, 2021 (9 pages) and English Version (8 pages).
Co-pending Japanese Application No. 2020-549630, English Version of Claims filed Nov. 27, 2020, 3 pages.
Co-pending Japanese Application No. 2020-549630, Office Action dated Jun. 21, 2021 (6 pages) and English Translation (7 pages).
Co-pending Japanese Application No. 2020-549630, Response to Jun. 21, 2021 Office Action, filed Nov. 19, 2021 (9 pages) and English Translation of the Amended Claims (4 pages).
Co-pending Korean Application No. 10-2020-7031999 Office Action dated Aug. 25, 2021 (10 pages) with English translation (9 pages).
Co-pending Korean Application No. 10-2020-7031999 Response to Aug. 25, 2021 Office Action, filed Nov. 25, 2021 (25 pages) with English translation of the amended claims (5 pages).
Co-pending Korean Application No. 10-2020-7031999 Voluntary Amendment filed Apr. 2, 2021 (15 pages) with English version of the amended claims (5 pages).
Halper, J.; Kjaer, M. (2014) Chapter 3: Progress in Heritable Soft Connective Tissue Diseases. Advances in Experimental Medicine and Biology, vol. 802, 26 pages.
Kumar, A. et al. Carbohydrate Polymers, "Application of xanthan gum as polysaccharide in tissue engineering: A review", published online Oct. 5, 2017, vol. 180 pp. 128-144.

(56) References Cited

OTHER PUBLICATIONS

Kunt, Emrah Deniz "Microfactory Concept with Bilevel Modularity" Graduate School of Engineering and Natural Sciences, Sabanci University, Fall 2011, 194 pages.
Shariati et al., (2015) Hydrogels for Cell Encapsulation and Bioprinting. In: Turksen K. (eds) Bioprinting in Regenerative Medicine. Stem Cell Biology and Regenerative Medicine. Springer, Cham., pp. 89-108.
Teelahti, Toimi "Implementing Additive Manufacturing in Microfactories." M.Sc. Thesis, Tampere University of Technology, 2014, 71 pages.
Tuan, R. S. et al., "Skin and Bones (and Cartilage): The Dermal Fibroblast Connection", NIH Public Access (pp. 1-5) of Nat Rev Rheumatol. 2009, 5(9): 471-472, 5 pages.
Turksen, K. (editor) Bioprinting in Regenerative Medicine. Stem Cell Biology and Regenerative Medicine. Springer, Cham., 2015, 148 pages.
(Abushall, Hany et al.) Co-Pending Application No. PCT/US19/19664, filed Feb. 26, 2019, Specification, Claims, Figures.
(Gatenholm, Paul) Co-pending U.S. Appl. No. 15/537,154, filed Jun. 16, 2017, Specification, Claims, Figures.
(Gatenholm, Paul) Co-pending U.S. Appl. No. 16/306,436, filed Nov. 30, 2018, Specification, Claims, Figures.
(Gatenholm, Paul) Co-pending U.S. Appl. No. 16/307,852, filed Dec. 6, 2018, Specification, Claims, Figures.
(Gatenholm, Paul) Co-pending U.S. Appl. No. 16/777,146, filed Jan. 30, 2020, Specification, Claims, Figures.
(Gatenholm, Paul) Co-pending U.S. Appl. No. 16/799,062, filed Feb. 24, 2020, Specification, Claims, Figures.
(Gatenholm, Paul) Co-pending European Application No. 17807642.8 filed Jan. 3, 2019, Specification, Claims, Figures.
(Gatenholm, Paul) Co-pending European Patent Application No. 17811137.3, filed Jan. 2, 2019, Claims (Attached), Specification, and Figures (See PCT/US17/036895).
(Gatenholm, Paul) Co-pending International Patent Application No. PCT/US15/66755 (APT-004-PCT) filed Dec. 18, 2015, published as WO 2016/100856 dated Jun. 23, 2016, Specification, Claims, Figures.
(Gatenholm, Paul) Co-pending International Patent Application No. PCT/US17/035861 filed Jun. 3, 2017, published as WO 2017/210663 dated Dec. 7, 2017, Specification, Claims, Figures.
(Gatenholm, Paul) Co-pending International Patent Application No. PCT/US17/036895, filed Jun. 9, 2017, which published as WO 2017/214592 dated Dec. 14, 2017, Specification, Claims, Figures.
(Gatenholm, Paul) Co-pending Japanese Application No. 2018-564332, filed on Dec. 7, 2018, Specification, Claims, and Figures (see PCT/US17/36895).
(Gatenholm, Paul) Co-pending Japanese Application No. 2019-516082 filed Nov. 30, 2018, Specification, Claims, Figures (see PCT/US17/35861).
(Martinez, Hector et al.) Co-Pending U.S. Appl. No. 17/048,755, filed Oct. 15, 2020, Specification, Claims, Figures.
(Martinez, Hector et al.) Co-pending International Application No. PCT/US19/55684, filed Oct. 10, 2019, Specification, Claims, Figures.
(Redwan, Adel Itadele Namro et al.) Co-pending International Application No. PCT/US19/58025, filed Oct. 25, 2019, Specification, Claims, Figures.
(Redwan, Adel Itedale Namro et al.) Co-Pending U.S. Appl. No. 16/979,452, filed Sep. 9, 2020, Specification, Claims, Figures.
(Redwan, Adele Itedale Namro et al.) Co-pending Japanese Application No. 2020-549630, filed Sep. 15, 2020, Specification, Claims, Figures (see PCT/US19/58025).
(Thayer, Patrick et al.) Co-Pending U.S. Appl. No. 16/964,899 filed Jul. 24, 2020, Specification, Claims, Figures.
(Thayer, Patrick et al.) Co-pending Application No. PCT/IB2019/000215, filed Jan. 25, 2019, Specification, Claims, and Figures.
Ahadian et al. "Bioconjugated Hydrogels for Tissue Engineering and Regenerative Medicine," Bioconjuoate Chem. Jul. 15, 2015 (Jul. 15, 2015) vol. 26, Iss. 10, pp. 1984-2001.
Andrade et al. "Improving the Affinity of Fibroblasts for Bacterial Cellulose Using.—Carbohydrate-Binding Modules Fused to RGD," Journal of Biomedical Materials Research. Jan. 22, 2009 (Jan. 22, 2009) vol. 92, Iss. 1, pp. 9-17.
Backdahl, H., Esguerra, M., Delbro, D., Risberg, B., and Gatenholm, P., Engineering microporosity in bacterial cellulose scaffolds, Journal of Tissue Engineering and Regenerative Medicine, 2 (6), 320-330 (2008).
Bovine Collagen Solution, Sigma Aldrich, 2020, https://www.sigmaaldrich.com/catalog/product/aldrich/804614?lang=en&region=US. (International Search Report of PCT/US2019/055684 dated Jan. 28, 2020 indicates this reference was retrieved as early as Jan. 6, 2020. Retrieved Apr. 14, 2020.).
Center for Drug Evaluation and Research (U.S.)., & Center for Drug Evaluation and Research (U.S.). (1985). Orange book: Approved drug products with therapeutic equivalence evaluations. Rockville, Md.: U.S. Dept. of Health and Human Services, Food and Drug Administration, Center for Drug Evaluation and Research, Office of Pharmaceutical Science, Office of Generic Drugs.
Co-pending U.S. Appl. No. 15/537,154 Non-Final Office Action dated Feb. 27, 2019, 6 pages.
Co-pending U.S. Appl. No. 15/537,154 Official Interview Summary dated Mar. 13, 2019, 3 pages.
Co-pending U.S. Appl. No. 15/537,154 Preliminary Amendment filed Jun. 16, 2017, 7 pages.
Co-pending U.S. Appl. No. 15/537,154 Response to Feb. 27, 2019 Non-Final Office Action, filed Mar. 18, 2019, 6 pages.
Co-pending U.S. Appl. No. 15/537,154 Response to Oct. 18, 2018 Restriction Requirement, dated Dec. 18, 2018, 7 pages.
Co-pending U.S. Appl. No. 15/537,154 Restriction Requirement dated Oct. 18, 2018, 8 pages.
Co-pending U.S. Appl. No. 16/306,436, Preliminary Amendment filed Nov. 30, 2018, 5 pages.
Co-pending U.S. Appl. No. 16/307,852, Preliminary Amendment filed Dec. 6, 2018, 8 pages.
Co-pending U.S. Appl. No. 16/777,146, Preliminary Amendment, filed Jan. 30, 2020, 5 pages.
Co-Pending U.S. Appl. No. 16/964,899 Preliminary Amendment filed Jul. 24, 2020, 6 pages.
Co-Pending U.S. Appl. No. 16/979,452, Preliminary Amendment filed Sep. 9, 2020, 8 pages.
Co-Pending U.S. Appl. No. 17/048,755, Preliminary Amendment filed Oct. 19, 2020, 7 pages.
Co-pending Application No. PCT/IB2019/000215, International Preliminary Report on Patentability, 14 pages.
Co-pending Application No. PCT/IB2019/000215, International Search Report and Written Opinion dated Feb. 9, 2019 and Written Opinion dated Jul. 4, 2019, 20 pages.
Co-Pending Application No. PCT/US19/19664, International Search Report and Written Opinion dated Jun. 6, 2019, 11 pages.
Co-pending European Patent Application No. 15871191.1 filed Jul. 18, 2017.
Co-pending European Patent Application No. 15871191.1, File History, dated Nov. 2019 to Feb. 2020, 30 pages.
Co-pending European Patent Application No. 15871191.1, File History, dated Oct. 2018 to Jul. 2019, 28 pages.
Co-pending European Patent Application No. 15871191.1, Letter and Communication pursuant to Rule 114(2) EPC, dated Jun. 12, 2018, 7 pages.
Co-pending European Patent Application No. 15871191.1, Supplemental Search and Opinion, dated Sep. 18, 2018, 8 pages.
Co-pending European Patent Application No. 17807642.8 Communication Pursuant to Rule 164(1) dated Jan. 27, 2020, 19 pages.
Co-pending European Patent Application No. 17807642.8 Communication Pursuant to Rules 161(2) and 162 EPC dated Feb. 1, 2019, 4 pages.
Co-pending European Patent Application No. 17807642.8 Response to Jan. 27, 2020 Communication Pursuant to Rule 164(1) filed Apr. 8, 2020, 3 pages.
Co-pending European Patent Application No. 17807642.8, Extended European Search Report dated Jun. 16, 2020, 21 pages.
Co-pending European Patent Application No. 17811137.3, Extended European Search Report dated Apr. 2, 2020, 9 pages.

(56) References Cited

OTHER PUBLICATIONS

Co-pending International Application No. PCT/US19/55684, International Search Report and Written Opinion dated Jan. 28, 2020, 8 pages.
Co-pending International Application No. PCT/US19/58025, International Search Report and Written Opinion dated Feb. 6, 2020, 10 pages.
Co-pending International Patent Application No. PCT/US15/66755, International Preliminary Report on Patentability dated Jun. 20, 2017, 6 pages.
Co-pending International Patent Application No. PCT/US15/66755, International Search Report and Written Opinion dated Apr. 28, 2016, 8 pages.
Co-pending International Patent Application No. PCT/US17/035861 filed Jun. 3, 2017, International Preliminary Report on Patentability dated Dec. 4, 2018, 11 pages.
Co-pending International Patent Application No. PCT/US17/035861 International Search Report and Written Opinion dated Aug. 17, 2017, 14 pages.
Co-pending International Patent Application No. PCT/US17/036895, International Preliminary Report on Patentability dated Aug. 17, 2017, 7 pages.
Co-pending International Patent Application No. PCT/US17/036895, International Search Report and Written Opinion dated Sep. 6, 2017, 9 pages.
Co-pending International Patent Application No. PCT/US2017/035861 filed Jun. 3, 2017, International Search Report and Written Opinion dated Aug. 17, 2017.
D. Gethin, A. Rees et al., "Studies on the 3D Printing of Nanocellulose Structures", Advances in Printing and Media Technology, vol. XLI(I), A2, (2014), 91-95.
Fink, Helen et al. Bacterial cellulose modified with xyloglucan bearing the adhesion peptide RGD promotes endothelial cell adhesion and metabolism—a promising modification for vascular grafts, Journal of Tissue Engineering and Regenerative Medicine, vol. 5, No. 6, Jun. 1, 2011, pp. 454-463.
Gatenholm P. et al. Bacteria fabricate 3D scaffolds for organ regeneration, Symposium 13: Biomedical research. New Biotechnology, Jul. 2014, vol. 31S, p. S52.
Goodman, L. S., Brunton, L. L., Chabner, B., & Knollmann, B. C. (2011). Goodman & Gilman'spharmacological basis of therapeutics. New York: McGraw-Hill.
Guerreiro, Susana G. et al. Neonatal Human Dermal Fibroblasts Immobilized in RGD-Alginate Induce Angiogenesis. Cell Transplantation, 23, 2014, 945-957.
Helenius G, H. Bäckdahl, A. Bodin, U. Nanmark, P. Gatenholm, B. Risberg, In vivo Biocompatibility of Bacterial Cellulose, J. Biomed. Mater. Res. A., 76, 431-438, 2005.
Huh et al. "From 3D Cell Culture to Organs-on-Chips," Trends Cell Biol. Dec. 1, 2011 (Dec. 1, 2011), vol. 21,155.12, pp. 745-754.
J.A. Rowley, G. Madlambayan, D.J Mooney, Alginate hydrogels as synthetic extracellular matrix materials, Biomaterials 20 (1999), 45-53.
Jia et al. "Engineering Alginate as a Bioink for Bioprinting," Acta Biomater. Oct. 1, 2015 (Oct. 1, 2015), vol. 10, Iss. 10, pp. 4323-4331.
Johnson, H. Y. Chung et al. Bio-ink properties and printability for extrusion printing living cells. Biomater. Sci. 2013, 1, 763-773.
Kuzmenko, Y, S. Saemfors, D. Haegg, and P. Gatenholm, Universal method for protein bioconjugation with nanocellulose scaffolds for increased cell adhesion. Mater. Sci. Eng., C,2013. 33(8): p. 4599-4607.
L.Nimeskern, et al., "Mechanical evaluation of bacterial nanocellulose as an implant material for ear cartilage replacement", Journal of the Mechanical Behaviour of Biomedical Materials, 22 (2013), 12-21.
Lee, K. Y. and Mooney, D. J. Alginate: Properties and biomedical applications. Progress in Polymer Science, 37, 2012, 106-126.

Markstedt et al. "3D Bioprinting Human Chondrocytes with Nanocellulose-Alginate Bioink—for Cartilage Tissue Engineering Applications," Bio Macromolecules, Mar. 25, 2015 (Mar. 25, 2015) vol. 16, Iss. 5, pp. 1489-1496.
Martinez Avila, Hector et al . . . 3D bioprinting of human chondrocyte-laden nanocellulose hydrogels for patient-specific auricular cartilage regeneration. Bioprinting. vol 1-2, Mar. 1, 2016, pp. 22-35.
Martinez, Hector Avila, S. Schwarz, E.M. Feldmann, A. Mantas, A. Von Bomhard, P. Gatenholm, and N. Rotter, Biocompatibility evaluation of densified bacterial nanocellulose hydrogel as an implant material for auricular cartilage regeneration. Appl. Microbiol. Biotechnol., 2014. 98(17): p. 7423-7435.
Michael, S. et al. Tissue Engineered Skin Substitutes Created by Laser-Assisted Bioprinting Form Skin-Like Structures in the Dorsal Skin Fold Chamber in Mice. PLOS. Mar. 4, 2013; vol. 8, No. 3, pp. 1-12; doi:10.1371/journal.pone.0057741.
Murphy S. V et al. 3D bioprinting of tissues and organs. Nature Biotechnology, Aug. 2014, vol. 32, No. 8, p. 773-785.
Nakamura et al. "Biomatrices and Biomaterials for Future Developments of Bioprinting and Biofabrication," Biofabrication, Mar. 10, 2010 (Mar. 10, 2010) vol. 2, Iss. 1, pp. 1-6.
O'Neil, M. J. (2006). The Merck index: An encyclopedia of chemicals, drugs, and biologicals. Whitehouse Station, N.J. Merck.
Panwar et al. "Current Status of Bioinks for Micro-Extrusion-Based 3D Bioprinting Molecules," Molecules, May 25, 2016 (May 25, 2016) vol. 21, Iss. 6, pp. 1-26.
Petersen N, Gatenholm, P., Bacterial cellulose-based materials and medical devices: current state and perspectives, Applied Microbiology and Biotechnology, 91, 1277, 2011.
Qing, Gao et al. Coxial nozzle-assisted 3D bioprinting with built-in microchannels for nutrients delivery. Biomaterials, 61, 2015, 203-215.
Remington, The Science and Practice of Pharmacy. Easton, Pa.: Mack Pub. Co., 1995.
Rutz et al. "A Multi-Material Bioink Method for 3D Printing Tunable, Cell-Compatible—Hydrogels," Adv Mater. Mar. 4, 2015 (Mar. 4, 2015), vol. 27, Iss. 9, pp. 1-18.
Salas, C et al. Nanocellulose properties and applications in colloids and interfaces. Current Opinion in Colloid and Interface Science. Oct. 30, 2014, vol. 19, No. 5, pp. 383-396.
United States Pharmacopeia and National Formulary. Rockville, MD: United States Pharmacopeial Convention; 2016.
Ventola C.L. Medical Applications for 3D Printing: Current and Projected Uses. P&T, Oct. 2014, vol. 39 No. 10, p. 704-711.
Xu, Mingen et al. An cell-assembly derived physiological 3D model of the metabolic syndrome, based on adipose-derived stromal cells and a gelatin/alginate/fibrinogen matrix. Biomaterials 31 (2010) 3868-3877.
Zhou, Y; The Application of Ultrasound in 3D Bio-Printing. Molecules. May 5, 2016, vol. 21 No. 590; pp. 1-25.
(Abushall, Hany et al.) Co-Pending European Application No. 19917298.2, filed Aug. 5, 2021, Specification, Claims, Figures (See WO 2020/176079).
(Boyer, Christen et al.) Co-pending U.S. Appl. No. 17/554,789, filed Dec. 17, 2021, Specification, Claims, Figures.
(Martinez, Hector et al.) Co-Pending Application No. PCT/US22/20148, filed Mar. 14, 2022, Specification, Claims, Figures.
(Redwan, Adel Itedale Namro et al.) Co-pending Japanese Application No. 2022-035620, filed Mar. 8, 2022, Specification, Claims, Figures (see PCT/US19/58025).
(Redwan, Adel Itedale Namro et al.) Co-pending Korean Application No. 10-2022-7017436 filed May 24, 2022, Specification, Claims, and Figures (See PCT/2019/058025 for English Translation).
Co-pending U.S. Appl. No. 16/306,436, Final Office Action dated May 17, 2022, 17 pages.
Co-pending U.S. Appl. No. 16/306,436, Response to Nov. 18, 2021 Non-Final Office Action, dated Feb. 17, 2022, 7 pages.
Co-pending U.S. Appl. No. 16/307,852, Restriction Requirement, dated Apr. 26, 2022, 9 pages.
Co-Pending U.S. Appl. No. 16/964,899 Non-Final Office Action, dated Apr. 14, 2022, 34 pages.
Co-Pending U.S. Appl. No. 16/979,452, Final Office Action dated Jun. 3, 2022, 15 pages.

(56) References Cited

OTHER PUBLICATIONS

Co-Pending U.S. Appl. No. 16/979,452, Non-Final Office Action dated Dec. 16, 2021, 16 pages.
Co-Pending U.S. Appl. No. 16/979,452, Response to Dec. 16, 2021 Non-Final Office Action, dated May 16, 2022, 15 pages.
Co-Pending European Application No. 19917298.2, Amended Claims filed Mar. 25, 2022, 13 pages.
Co-pending European Patent Application No. 19874873.3, Extended European Search Report, dated Feb. 8, 2022, 10 pages.
Co-pending Japanese Application No. 2018-564332 Certificate of Patent 7053503, date of registration Apr. 4, 2022, 2 pages.
Co-pending Japanese Application No. 2019-516082, Final Office Action dated Dec. 16, 2021 (3 pages) and English Translation (4 pages).
Co-pending Japanese Application No. 2019-516082, Response to Dec. 16, 2021 Final Office Action, dated Jun. 17, 2022 (9 pages) and English Translation (9 pages).
Co-pending Japanese Application No. 2020-549630, Office Action dated Apr. 18, 2022 (4 pages) and English Translation (5 pages).
Co-pending Japanese Application No. 2020-549630, Office Action dated Dec. 9, 2021 (4 pages) and English Translation (4 pages).
Co-pending Japanese Application No. 2020-549630, Response to Dec. 9, 2021 Office Action, filed Mar. 9, 2022 (6 pages) and English Translation of the Amended Claims (4 pages).
Co-pending Korean Application No. 10-2020-7031999 Office Action dated Feb. 23, 2022 (4 pages) with English translation (3 pages).
Co-pending Korean Application No. 10-2022-7017436, Remarks and Claims as filed (11 pages) dated May 24, 2022, with English version (9 pages).
Memic, Adnan et al. "Bioprinting technologies for disease modeling", Biotechnol Lett (2017) 39:1279-1290, 12 pages.
Schuurman, W. et al., Macromolecular Bioscience, "Gelatin-Methacrylamide Hydrogels as Potential Biomaterials for Fabrication of Tissue-Engineered Cartilage Constructs", 2013, vol. 13, pp. 551-561.
Zhao, Yu et al. "Three-dimensional printing of Hela cells for cervical tumor model in vitro", Biofabrication, 6, 2014, 035001, 10 pages.
Co-pending U.S. Appl. No. 16/307,852, Election of Species Requirement, dated Oct. 5, 2022, 7 pages.
Co-pending U.S. Appl. No. 16/307,852, Response to Apr. 26, 2022 Restriction Requirement, dated Aug. 22, 2022, 5 pages.
Co-Pending U.S. Appl. No. 16/964,899 Final Office Action, dated Oct. 6, 2022, 22 pages.
Co-Pending U.S. Appl. No. 16/964,899 Response to Non-Final Office Action, dated Sep. 12, 2022, 7 pages.
Co-Pending U.S. Appl. No. 16/979,452, Response to Jun. 3, 2022 Final Office Action, dated Sep. 6, 2022, 11 pages.
Co-Pending Application No. PCT/US22/20148, International Search Report and Written Opinion dated Jun. 29, 2022, 13 pages.
Co-pending European Patent Application No. 19874873.3, Response to the Feb. 25, 2022 Communication Pursuant to Rules 70(2) and 70a(2) EPC, dated Sep. 7, 2022, 11 pages.
Co-pending Japanese Application No. 2020-549630, Office Action dated Aug. 18, 2022 (3 pages) and English Translation (4 pages).
Co-pending Japanese Application No. 2020-549630, Response to Apr. 18, 2022 Office Action, dated Jul. 15, 2022 (6 pages) and English Version (6 pages).
(Redwan, Adel Itedale Namro et al.) Co-pending Japanese Application No. 2023-064856, filed Apr. 12, 2023, Specification, Claims, Figures (see PCT/US19/58025).
Co-pending U.S. Appl. No. 16/307,852, Non-Final Office Action, dated Feb. 6, 2023, 15 pages.
Co-pending U.S. Appl. No. 16/307,852, Response to Oct. 5, 2022 Election of Species Requirement, dated Dec. 5, 2022, 5 pages.
Co-pending U.S. Appl. No. 16/799,062, Non-Final Office Action dated Mar. 10, 2023, 7 pages.
Co-pending U.S. Appl. No. 16/799,062, Response to Jan. 5, 2023 Restriction Requirement dated Jan. 18, 2023, 2 pages.
Co-pending U.S. Appl. No. 16/799,062, Response to Mar. 10, 2023 Non-Final Office Action, dated Mar. 15, 2023, 6 pages.
Co-pending U.S. Appl. No. 16/799,062, Restriction Requirement dated Jan. 5, 2023, 6 pages.
Co-Pending U.S. Appl. No. 16/964,899 Response to Oct. 6, 2022 Final Office Action, dated Jan. 9, 2023, 10 pages.
Co-Pending U.S. Appl. No. 16/979,452, Final Office Action dated Mar. 23, 2023, 16 pages.
Co-Pending U.S. Appl. No. 16/979,452, Non-Final Office Action dated Oct. 26, 2022, 14 pages.
Co-Pending U.S. Appl. No. 16/979,452, Response to Oct. 26, 2022 Non-Final Office Action, dated Feb. 23, 2023, 8 pages.
Co-pending U.S. Appl. No. 17/554,789, Non-Final Office Action dated Feb. 9, 2023, 11 pages.
Co-Pending European Application No. 19917298.2, Extended European Search Report dated Sep. 8, 2022, 9 pages.
Co-pending European Patent Application No. 19874873.3, Communication pursuant to Article 94(3) EPC, dated Dec. 8, 2022, 6 pages.
Co-pending Japanese Application No. 2019-516082, Decision to Grant dated Oct. 26, 2022, 4 pages.
Co-pending Japanese Application No. 2020-549630, Decision of Rejection dated Dec. 12, 2022 (1 page) and English Translation (2 pages).
Co-pending Japanese Application No. 2020-549630, Response to Aug. 18, 2022 Office Action dated Nov. 4, 2022 (7 pages) and English Translation of the claims (3 pages).
Co-pending Japanese Application No. 2020-549630, Response to Dec. 12, 2022 Decision of Rejection, dated Apr. 12, 2023 (7 pages) and English Translation of the Amended Claims (3 pages).
Co-pending Japanese Application No. 2022-035620, Voluntary Amendment dated Oct. 24, 2022 (5 pages) and English Translation of the Claims (10 pages).
Fine et al. "The Effect of Transforming Growth Factor-beta on Cell Proliferation and Collagen Formation by Lung Fibroblasts." JBC (1987), 262(8), p. 3897-3902.
Koch et al. "Skin Tissue Generation by Laser Cell Printing." Biotechnology and Bioengineering (2012); 109, 1855-1863.
Co-pending U.S. Appl. No. 16/307,852, Final Office Action, dated Jun. 9, 2023, 14 pages.
Co-pending U.S. Appl. No. 16/307,852, Response to Feb. 6, 2023 Non-Final Office Action, dated May 5, 2023, 7 pages.
Co-pending U.S. Appl. No. 16/799,062, Notice of Allowance dated May 24, 2023, 7 pages.
Co-pending European Patent Application No. 19874873.3, Response to Dec. 8, 2022 Communication pursuant to Article 94(3) EPC, dated Jun. 19, 2023, 20 pages.
Co-pending Japanese Application No. 2023-064856, Voluntary Amendment and Request for Examination dated May 11, 2023 (52 pages) and English Translation of the Amended Claims (4 pages).
Hinton et al. "Three-dimensional printing of complex biological structures by freeform reversible embedding of suspended hydrogels." Sci. Adv. (Oct. 2015), 1, e1500758, plus appended supplementary information. (2015), 25 pages.
(Gatenholm, Paul) Co-pending U.S. Appl. No. 18/455,533, filed Aug. 24, 2023, Specification, Claims, Figures.
(Martinez, Hector et al.) Co-Pending U.S. Appl. No. 18/550,279, filed Sep. 12, 2023, Specification, Claims, and Figures.
Co-pending U.S. Appl. No. 16/777,146, Response to Aug. 4, 2023 Restriction Requirement, dated Oct. 4, 2023, 5 pages.
Co-pending U.S. Appl. No. 16/777,146, Restriction Requirement dated Aug. 4, 2023, 6 pages.
Co-Pending U.S. Appl. No. 16/979,452, Non-Final Office Action dated Oct. 3, 2023, 15 pages.
Co-Pending U.S. Appl. No. 16/979,452, Response to Mar. 23, 2023 Final Office Action, dated Aug. 23, 2023, 9 pages.
Co-pending U.S. Appl. No. 17/554,789, Final Office Action dated Oct. 2, 2023, 12 pages.
Co-pending U.S. Appl. No. 17/554,789, Response to Feb. 9, 2023 Non-Final Office Action, dated Aug. 9, 2023, 9 pages.

* cited by examiner

TEMPERATURE-CONTROLLED MULTI-MATERIAL OVERPRINTING

CROSS-REFERENCE TO RELATED APPLICATIONS

The present application relies on the disclosure of and claims priority to and the benefit of the filing date of U.S. Provisional Patent Application No. 62/897,188 filed Sep. 6, 2019, which is hereby incorporated by reference herein in its entirety.

BACKGROUND OF THE INVENTION

Field of the Invention

The present invention is directed to the field of three-dimensional (3D) bioprinting. More particularly, embodiments of the invention are directed to systems and methods which utilize digital light processing (DLP) and multiple bioink resin tanks containing one or more photopolymerizable resins to provide for multi-material overprinting on a printing surface.

Description of Related Art

In order to replicate complex tissue structures such as organs, it is desirable to build tissue strata having constituents and properties which differ from previous layers. Current technologies for 3D bioprinting including extrusion, inkjet, acoustic/ultrasound, laser, and stereolithography technologies fall short of this goal. Thus, new technologies for 3D bioprinting are urgently needed.

SUMMARY OF THE INVENTION

Toward this end, a method of three-dimensional (3D) bioprinting is disclosed, which method includes immersing a printing platform or surface into a first bioink resin, curing one or more layer of the first bioink resin onto the printing platform or surface, and removing the printing platform or surface from the first bioink resin. The process is repeated with a second bioink resin such that the second bioink resin is cured on top of the one or more layer of first bioink resin, and can be further repeated with a third or even fourth bioink resin. By varying the composition of one or more or each bioink resin such as living cell type or polymer, complex, multilayered tissues can be engineered.

A system for three-dimensional (3D) bioprinting is also disclosed which is capable of performing the above method. The system includes a printing platform or surface, first and second container, one or more source of electromagnetic radiation, one or more actuator capable of horizontal, vertical, and/or rotary movement of the printing platform or surface and/or first container and/or second container and/or one or more source of electromagnetic radiation, and a controller capable of sending commands to the one or more source of electromagnetic radiation and one or more actuator.

Embodiments include Aspect 1, which is a method of three-dimensional (3D) bioprinting comprising immersing a printing platform or surface into a first bioink resin, curing one or more layer of the first bioink resin on the printing platform or surface, and removing the printing platform or surface from the first bioink resin.

Aspect 2 is a method of three-dimensional (3D) bioprinting comprising mechanically lowering a printing platform or surface into a first container irradiating the printing platform or surface with electromagnetic energy, and mechanically raising the printing platform or surface from the first container.

Aspect 3 is the method of Aspect 1, further comprising immersing the printing platform or surface into a second bioink resin; and curing one or more layer of the second bioink resin.

Aspect 4 is the method of Aspect 2, further comprising mechanically lowering the printing platform or surface into a second container.

Aspect 5 is the method of Aspect 4, further comprising irradiating the printing platform or surface with electromagnetic energy.

Aspect 6 is the method of any one of Aspects 2, 4, or 5, wherein the first container comprises a first bioink resin and the second container comprises a second bioink resin.

Aspect 7 is the method of Aspect 6, wherein the electromagnetic energy is capable of curing one or more layer of the first bioink resin and/or second bioink resin.

Aspect 8 is the method of any of Aspects 1-7, wherein the first bioink resin is the same as the second bioink resin.

Aspect 9 is the method of any of Aspects 1-8, wherein the first bioink resin is different from the second bioink resin.

Aspect 10 is the method of any of Aspects 1-9, wherein curing one or more layer of the first and/or second bioink resin comprises polymerizing one or more monomer within the first and/or second bioink resin.

Aspect 11 is the method of any of Aspects 1-10, further comprising irradiating the printing platform or surface or a portion thereof with electromagnetic energy to initiate curing of the first and/or second bioink resin and/or polymerization of the one or more monomer.

Aspect 12 is the method of any of Aspects 1-11, wherein the electromagnetic energy comprises light.

Aspect 13 is the method of any of Aspects 1-12, wherein curing one or more layer of the first and/or second bioink resin comprises irradiating the first and/or second bioink resin with light from one or more digital light processing (DLP) projector.

Aspect 14 is the method of any of Aspects 1-13, wherein the light is ultraviolet, visible, or infrared.

Aspect 15 is the method of any of Aspects 1-14, wherein curing one or more layer of the first and/or second bioink resin comprises photopolymerization of a monomer to form one or more polymer.

Aspect 16 is the method of any of Aspects 1-15, wherein the one or more polymer is a biopolymer.

Aspect 17 is the method of any of Aspects 1-16, wherein the one or more polymer is a synthetic polymer.

Aspect 18 is the method of any of Aspects 1-17, wherein the polymer formed from the first bioink resin is the same as the polymer formed from the second bioink resin.

Aspect 19 is the method of any of Aspects 1-18, wherein the polymer formed from the first bioink resin is different from the polymer formed from the second bioink resin.

Aspect 20 is the method of any of Aspects 1-19, wherein photopolymerization is initiated by one or more photoinitiator present in the first and/or second bioink resin.

Aspect 21 is the method of any of Aspects 1-20, wherein photopolymerization is controlled by one or more photoabsorber present in the first and/or second bioink resin.

Aspect 22 is the method of any of Aspects 1-21, wherein the first bioink resin and/or second bioink resin comprises one or more living cells.

Aspect 23 is the method of any of Aspects 1-22, wherein the living cells of the first bioink resin are the same as the living cells of the second bioink resin.

Aspect 24 is the method of any of Aspects 1-23, wherein the living cells of the first bioink resin are different from the living cells of the second bioink resin.

Aspect 25 is the method of any of Aspects 1-24, wherein the first bioink resin and/or second bioink resin comprises one or more therapeutic agents or particles.

Aspect 26 is the method of any of Aspects 1-25, wherein the one or more therapeutic agents or particles of the first bioink resin are the same as the one or more therapeutic agents or particles of the second bioink resin.

Aspect 27 is the method of any of Aspects 1-26, wherein the one or more therapeutic agents or particles of the first bioink resin are different from the one or more therapeutic agents or particles of the second bioink resin.

Aspect 28 is the method of any of Aspects 1-27, wherein the one or more therapeutic agents or particles comprise a biologic.

Aspect 29 is the method of any of Aspects 1-28, wherein the one or more therapeutic agents or particles comprise a small molecule.

Aspect 30 is the method of any of Aspects 1-29, further comprising immersing the printing platform or surface into a third bioink resin and curing one or more layer of the third bioink resin.

Aspect 31 is the method of any of Aspects 1-30, wherein the immersing and removing of the printing platform or surface or mechanically lowering and mechanically raising of the printing platform or surface is by way of one or more actuator.

Aspect 32 is the method of any of Aspects 1-31, wherein the one or more actuator is/are capable of rotary and/or vertical motion.

Aspect 33 is the method of any of Aspects 1-32, further comprising consecutively positioning the first bioink resin and second bioink resin or first container and second container below the printing platform or surface.

Aspect 34 is the method of any of Aspects 1-33, wherein the consecutive positioning is by way of one or more actuator.

Aspect 35 is the method of any of Aspects 1-34, wherein the one or more actuator is capable of rotary and/or horizontal motion.

Aspect 36 is the method of any of Aspects 1-35, wherein immersing the printing platform or surface into the first bioink resin comprises mechanically lowering the printing platform or surface into the first container.

Aspect 37 is the method of any of Aspects 1-36, wherein curing the one or more layer of the first bioink resin on the printing platform or surface comprises irradiating the printing platform or surface with electromagnetic energy.

Aspect 38 is the method of any of Aspects 1-37, wherein removing the printing platform or surface from the first bioink resin comprises mechanically raising the printing platform or surface from the first container.

Aspect 39 is the method of any of Aspects 1-38, wherein immersing the printing platform or surface into the second bioink resin comprises mechanically lowing the printing platform or surface into the second container.

Aspect 40 is the method of any of Aspects 1-39, wherein the first container is mechanically removed and the second container is mechanically positioned below the printing platform or surface prior to lowering.

Aspect 41 is the method of any of Aspects 1-40, wherein the printing platform or surface is inflatable and optionally further comprising inflating or deflating the printing platform or surface.

Aspect 42 is the method of any of Aspects 1-41, further comprising controlling the temperature of the printing platform or surface or first and second bioink resin or first and second container by way of one or more temperature control unit.

Aspect 43 is a system for three-dimensional (3D) bioprinting comprising a printing platform or surface, first and second containers, one or more source of electromagnetic radiation, one or more actuator capable of horizontal, vertical, and/or rotary movement of the printing platform or surface and/or the first container and/or second container and/or the one or more source of electromagnetic radiation, and a controller capable of sending commands to the one or more source of electromagnetic radiation and the one or more actuator.

Aspect 44 is the system of Aspect 43, or a method, wherein the system is configured to perform or the method comprises the steps of:
  a) positioning the first container below the printing platform or surface; and/or
  b) mechanically lowering the printing platform or surface into the first container; and/or
  c) irradiating the printing platform or surface with electromagnetic energy; and/or
  d) mechanically raising the printing platform or surface from the first container; and/or
  e) positioning the second container below the printing platform or surface; and/or
  f) mechanically lowering the printing platform or surface into the second container; and/or
  g) irradiating the printing platform or surface with electromagnetic energy; and/or
  h) mechanically raising the printing platform or surface from the second container.

Aspect 45 is the system or method of Aspect 44, wherein the system is configured to perform or the method comprises the steps of any of steps a through h consecutively, such as steps a and b, steps a through c, steps a through d, steps a through e, steps a through f, steps a through g, or steps a thorough h.

Aspect 46 is the system of Aspect 43, wherein the one or more actuator is configured to raise and lower the printing platform or surface by way of vertical and/or rotary motion and position the first container or second container below the printing platform or surface by way of horizontal and/or rotary motion.

Aspect 47 is the system of any of Aspects 43-46, wherein the one or more actuator comprises one or more linear or rotary actuators.

Aspect 48 is the system of any of Aspects 43-47, wherein the one or more actuators are pneumatic, hydraulic, electric and/or mechanical actuators.

Aspect 49 is the system of Any of Aspects 43-48, wherein the system is configured to perform the method of any preceding claim.

Aspect 50 is the system of any of Aspects 43-49, wherein the one or more source of electromagnetic energy is one or more light source, optionally one or more digital light processing (DLP) projector.

Aspect 51 is the system of any of Aspects 43-50, wherein the controller comprises one or more processor and a non-transitory computer readable storage medium comprising one or more 3D files having instructions capable of being read by the processor.

Aspect 52 is the system of any of Aspects 43-51, wherein the electromagnetic energy is light, such as UV, visible, or infrared light.

Aspect 53 is the system of any of Aspects 43-52, wherein the one or more digital light processing (DLP) projector are positioned or positionable above, below, and/or at one or more sides of the printing platform or surface and/or first and/or second container.

Aspect 54 is the system of any of Aspects 43-53, wherein the printing platform or surface is capable of inflation or deflation.

Aspect 55 is the system of any of Aspects 43-54, further comprising a tank of compressed air or inert gas or air or inert gas compression mechanism.

Aspect 56 is the system of any of Aspects 43-55, further comprising one or more temperature control unit in operable communication with the printing platform or surface and/or first and/or second containers and/or a platform or stage holding the first and/or second containers.

Aspect 57 is the system or method of any of Aspects 1-56, which incorporates structure or methods step(s) for extruding bioink.

BRIEF DESCRIPTION OF THE DRAWINGS

The accompanying drawings illustrate certain aspects of embodiments of the present invention, and should not be used to limit the invention. Together with the written description the drawings serve to explain certain principles of the invention.

DETAILED DESCRIPTION OF VARIOUS EMBODIMENTS OF THE INVENTION

Figure 1:
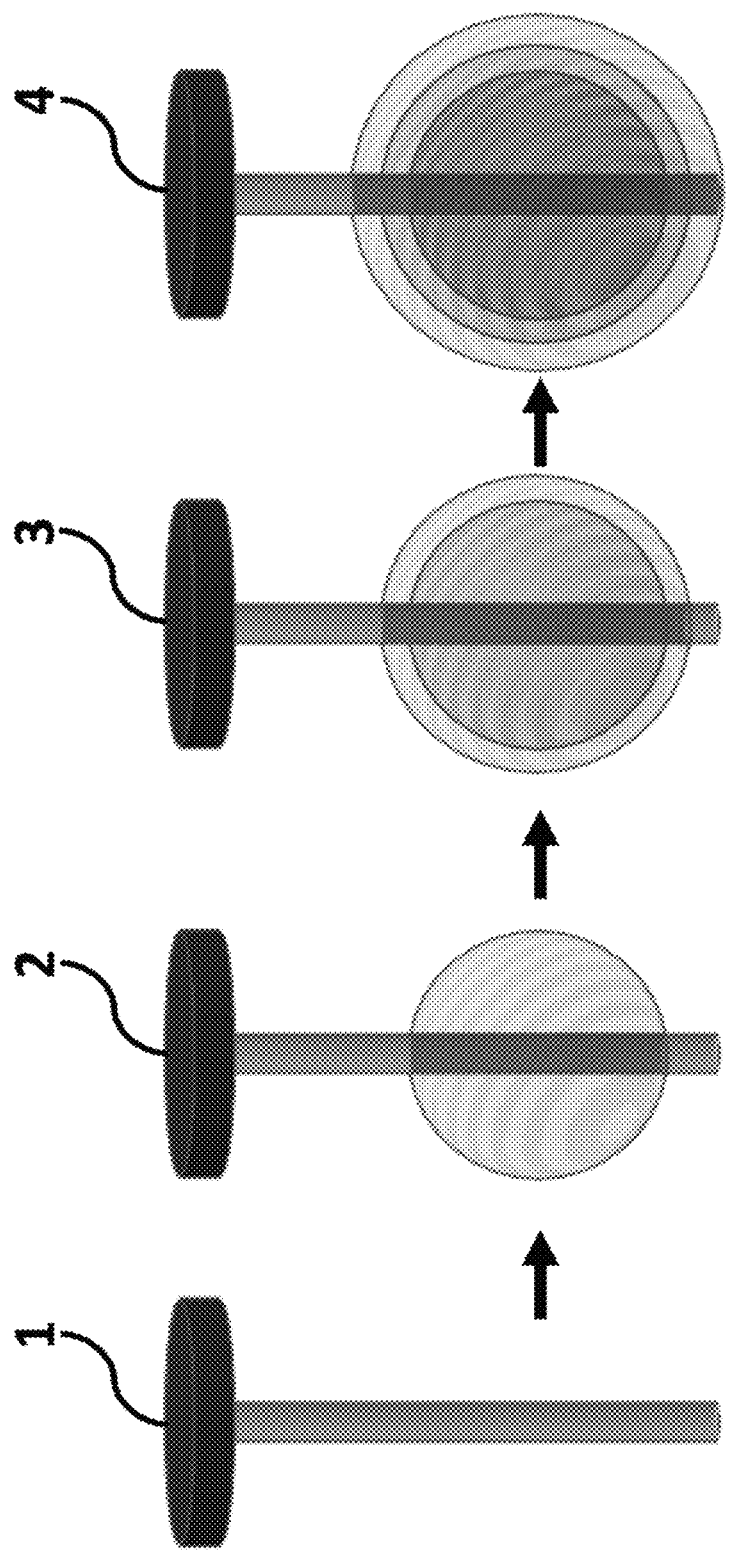
FIG. 1 is a schematic diagram showing a print surface and the progression of different bioinks photocured on the surface with a side projector according to an embodiment.

Reference will now be made in detail to various exemplary embodiments of the invention. It is to be understood that the following discussion of exemplary embodiments is not intended as a limitation on the invention. Rather, the following discussion is provided to give the reader a more detailed understanding of certain aspects and features of the invention.

As used herein, "digital light processing", or "DLP" is a 3D printing process in which a projector is used to emit electromagnetic energy such as light to cure a resin.

As used herein, "computed axial lithography", or "CAL" is a volumetric additive manufacturing process which relies on DLP to deliver a computed 3D exposure dose to a rotating volume of photopolymerizable resin, thereby producing a 3D object.

As used herein, a "resin" or "bioink resin" is a reagent containing one or more photopolymerizable monomers, photo-initiators, photo-absorbers, living cells, and other constituents which together contribute to the formation of bioprinted tissue.

As used herein, "DLP/CAL printing" or "DLP/CAL" is a process which incorporates DLP and CAL and two or more bioink resin tanks to form multi-layered tissue structures.

As used herein, "printing platform", "printing surface", "overprinting surface", and the like are used interchangeably to indicate a substrate upon which one or more bioink resin is cured.

According to one embodiment, a temperature controlled multi-bioink resin tank system for 3D bio-overprinting through DLP/CAL includes two or more tunable temperature controlled bioink resin tanks which are used consecutively to form a multi-layered tissue which is overprinted on a surface based on instructions stored in 3D files or software and tasks executed by a controller. The multi-layer tissue is formed by overprinting on a printing surface submerged in the bioink resin tank through one or more DLP projectors which cure the resin on the surface, which projectors can be positioned from the top, side and/or beneath the bioink resin tank or any angle therebetween. The one or more DLP projectors can be stationary or can be moveable by one or more actuators. The overprinting surface can be an inflatable, soft, or solid 3D shape, or combination thereof, and can include a rubber polymer, plastic, or metal, or combination thereof. The overprinting surface can be moveable by one or more actuators capable of rotary or vertical movement, and can have an extrusion function. The extrusion function can be implemented for example by way of one or more ports or orifices disposed in communication with one or more print surface and channels, such as the orifice being disposed on the top of the print surface and the channel(s) being disposed underneath the print surface. The channels can deliver one or more bioink, such as extrudable bioinks, including gels or polymers, which are capable of being extruded, for example into a photopolymerizable gel. For example, one or more materials can be dispensed by way of a sprayer, or other device for dispensing materials without direct contact with the printed structures and/or the print surface. In one embodiment, an air-brush type sprayer can be used that can spray additional cells, drugs, nanofibers, etc. between layers or around the printed structures. Such dispensing/extrusion function, shown in FIG. 5, will be elaborated on further below. The two or more tunable temperature controlled bioink resin tanks can be used consecutively as a solution rinse step or solution absorb step during the process. The two or more tunable temperature controlled bioink resin tanks can mechanically rotate into position below the overprinting surface which is raised and lowered in one or more or each bioink resin tank to form a multi-layered tissue through DLP/CAL printing. Further, the two or more bioink resin tanks can have tunable temperature control for biologics, cells, biopolymers, synthetic polymers, therapeutics or any combination thereof. The temperature control for one or more or each bioink resin tank can be in the range of 4 to 60 degrees Celsius. The temperature controlled bioink resin tank(s) can include a condensation absorber. The two or more bioink resin tanks can include one or more bioinks with one or more natural or synthetic monomers capable of polymerization by way of electromagnetic irradiation, one or more types of living cells, one or more therapeutic agents or particles, and one or more photo-initiators or photo-absorbers. The completed bio-overprinting tissue structure can be removed from the surface by way of deflation according to some embodiments. The completed bio-overprinting tissue structure can also be used as a bioreactor with inflating or deflating mechanical forces on the bioprinted tissue according to some embodiments. The system can include a clean chamber function using positive pressure of filtered air or inert gas.

The temperature controlled multi-bioink resin tank system includes a controller and one or more DLP/CAL projector, as well as one or more actuators to control motion of a print platform or surface, the bioink resin tanks, and/or one or more DLP/CAL projector such that different bioink resins can be cured on the print surface consecutively to form a multi-layered tissue on the print surface. The controller commands the one or more DLP/CAL projector and the actuators to allow for bioprinting on the print surface.

The electromagnetic energy from the DLP/CAL projector can have a wavelength ranging from 100 nm to 2,500 nm, including from 250 nm to 450 nm, or from 300 nm to 425 nm, or from 330 nm to 420 nm, or from 350 nm to 390 nm, or from 365 nm to 405 nm, or from 330 and 460 nm, or from 370 and 440 nm, or from 405 nm to 500 nm, or from 500 nm to 800 nm, or from 700 nm to 2,500 nm.

The electromagnetic energy from the DLP/CAL projector can include UV light with wavelengths ranging from 100 nm to 400 nm, including UV-A light (320-400 nm), UV-B light (290-320 nm), and UV-C light (100-290 nm). The electromagnetic energy can include infrared light with wavelengths ranging from 780 nm to 1 mm, including IR-A (780 nm-1.4 µm), IR-B (1.4-3 µm) and IR-C, also known as far-IR (3 µm-1 mm). The electromagnetic energy can include visible light with wavelengths ranging from 400 nm to 700 nm.

The intensity of the electromagnetic energy from the DLP/CAL projector can range from 0.1-40 $J/cm^2$ such as from 0.1-1 $J/cm^2$, 1-5 $J/cm^2$, 5-10 $J/cm^2$, 10-15 $J/cm^2$, 15-20 $J/cm^2$, 20-25 $J/cm^2$, 25-30 $J/cm^2$, 30-35 $J/cm^2$, or 35-40 $J/cm^2$. The frequency of the electromagnetic energy used for irradiation can be varied. For example, ultraviolet light has frequencies that range from $8\times10^{14}$ Hz to $3\times10^{16}$ Hz. If infrared light is used, the frequency can range from 300 GHz to 450 THz.

The source of the electromagnetic energy from the DLP/CAL projector can be a laser, LED, incandescent, or fluorescent light source. Depending upon the desired wavelength, the laser can be a solid-state laser, gas laser, excimer laser, dye laser, or semiconductor laser.

The controller can perform operations and processes described or depicted herein through one or more computer processor. For example, the one or more computer processor can issue commands to the DLP/CAL projector to irradiate the overprinting surface with a specified wavelength, intensity, and location. Further, the one or more computer processor can issue commands to the actuators to control horizontal, vertical, or rotary motion of the bioink resin tanks, overprinting surface, or one or more DLP/CAL projector as well as inflation and deflation of the print surface (if such inflatable surface is implemented). The one or more computer processor commands a sequence of movements such that a different bioink from one or more or each tank can be used to photopolymerize a layer on the overprinting surface.

The one or more computer processor commands the DLP/CAL projector and actuators through instructions programmed on one or more computer files which are read by the one or more computer processors. Embodiments can include a non-transitory computer readable storage medium comprising one or more computer files (e.g. "3D files") comprising a set of computer-executable instructions for performing one or more of the processes and operations described herein and/or depicted in the drawings, such as irradiation of the overprinting surface by the DLP/CAL projector or movement of the actuators. The 3D files can be created through Computer Aided Design (CAD) software, or equivalent 3D modeling software, which allow a user to determine the 3D structure of the overprinted tissue by creating tissue structure models. In embodiments, the files can be stored contiguously or non-contiguously on the computer-readable medium. Further, embodiments include a computer program product comprising the computer files, either in the form of the computer-readable medium comprising the computer files and, optionally, made available to a consumer through packaging, or alternatively made available to a consumer through electronic distribution. As used herein, a "computer-readable medium" includes any kind of computer memory such as floppy disks, conventional hard disks, CD-ROMS, Flash ROMS, non-volatile ROM, electrically erasable programmable read-only memory (EEPROM), and RAM.

As used herein, the terms "computer-executable instructions", "code", "software", "program", "application", "software code", "computer readable code", "software module", "module" and "software program" are used interchangeably to mean software instructions that are executable by a processor. The computer-executable instructions can be organized into routines, subroutines, procedures, objects, methods, functions, or any other organization of computer-executable instructions that is known or becomes known to a skilled artisan in light of this disclosure, where the computer-executable instructions are configured to direct a computer or other data processing device to perform one or more of the specified processes and operations described herein. The computer-executable instructions can be written in any suitable programming language, non-limiting examples of which include C, C++, C#, Objective C, Swift, Ruby/Ruby on Rails, Visual Basic, Java, Python, Perl, PUP, and JavaScript.

In other embodiments of the invention, files comprising the set of computer-executable instructions can be stored in computer-readable memory on a single computer or distributed across multiple computers. A skilled artisan will further appreciate, in light of this disclosure, how the invention can be implemented, in addition to software, using hardware or firmware. As such, as used herein, the operations of the invention can be implemented in a system comprising any combination of software, hardware, or firmware.

Embodiments of the invention include one or more computers or devices loaded with a set of the computer-executable instructions described herein. The computers or devices can be a general-purpose computer, a special-purpose computer, or other programmable data processing apparatus to produce a particular machine, such that the one or more computers or devices are instructed and configured to carry out the processes and operations described herein. The computer or device performing the specified processes and operations can comprise at least one processing element such as a central processing unit (i.e. processor) and a form of computer-readable memory which can include random-access memory (RAM) or read-only memory (ROM). The computer-executable instructions can be embedded in computer hardware or stored in the computer-readable memory such that the computer or device can be directed to perform one or more of the processes and operations depicted in the drawings and/or described herein. The computer-executable instructions can provide an operator interface for the system controller which can be a graphical user interface (GUI) which can be presented on a display of a general-purpose or special-purpose computer with a processor, computer-readable memory, and standard I/O interfaces such as a universal serial bus (USB) port and a serial port, a disk drive, a CD-ROM drive, and/or one or more user interface devices including a keyboard, keypad, mouse, control panel, touch screen display, microphone, etc. which allow a user to operate or program the controller.

The actuators controlling the movement of system components can include rotary actuators, such as for mechanical rotation of the bioink resin tanks or the overprinting surface, or linear actuators such as for mechanical raising and lowering of the overprinting surface from and to the interior of the bioink resin tanks. The actuators can be pneumatic, hydraulic, electric or mechanical actuators.

The system can include one or more temperature control units which are capable of regulating the temperature of the bioink resin tanks. In some embodiments, the temperature of the overprinting surface is independently controlled through a temperature control unit. The temperature control units can include a heater in communication with the bioink resin tanks, or a heat sink such as circulating coolant. The temperature control units are capable of regulating the temperature of the bioink resin tanks in the range of 4 to 60 degrees Celsius.

The system can include one or more tanks of pressurized air or inert gas such as nitrogen or helium for inflation of the overprinting surface or for cleaning any component of the system.

The system and its components can be powered via 60V or 120V AC current, or other voltages according to the single-phase voltage standard that is used in particular countries or regions. In general, this can be in the range of 100-127 volts or 220-240 volts.

One or more bioink resin tank can include one or more natural, semi-synthetic or synthetic monomers which, upon irradiation with electromagnetic energy for example from one or more DLP/CAL projector, can form a polymer such as any biodegradable or non-biodegradable, optionally "biocompatible polymer," which when introduced into a living system is compatible with living tissue and/or the living system (e.g., not substantially toxic, injurious, or leading to immunological rejection). Any target polymer can be used, including any monomers, co-polymers, and block co-polymers used for preparing any such target polymer.

One or more bioink resin tank can include one or more natural monomers which, upon irradiation with electromagnetic energy for example from one or more DLP/CAL projector, form a polymer or biopolymer such as gelatin, alginate, fibrin, hyaluronic acid (or hyaluronan), agarose, decellularized extracellular matrix, silk, natural rubber, glycogens, chitin, amylopectin, cellulose, alginate, wool, amber, keratin, collagen, starch, DNA, shellac, growth factors, Matrigel®, poly (acrylic acid), polypeptide-DNA, anticoagulants (including heparin and coumarin), polysaccharide, dextran, casein, albumin, ovalbumin, fibronectin, keratin, pectin, or elastin. Particular examples of photopolymerizable bioinks that can be used include gelatin methacrylate, collagen methacrylate, and PEGDA.

One or more bioink resin tank can include one or more semi-synthetic or synthetic monomers which, upon irradiation with electromagnetic energy for example from one or more DLP/CAL projector, can form a polymer or biopolymer, for example, including polymethylmethacrylate, polyaryletherketones (PAEKs), including polyetheretherketone (PEEK) and polyaryletherketone-etherketoneketone (PEKEKK), polyurethane, poly(L-lactide), poly(D,L-lactide), poly(L-co-D,L-lactide), polyglycolide, poly(lactide-co-glycolide), poly(hydroxylbutyrate), poly(hydroxyvalerate), tyrosine-derived polycarbonate, polyanhydride, polyorthoester, polyphosphazene, poly(dioxanone), poly(ε-caprolactone), and polyglyconate, such as described in U.S. Pat. No. 9,662,821, which is hereby incorporated by reference herein in its entirety. Other similar polymers known in the art may be used and various combinations of polymers may be included in the composition to adjust the properties of the composition as desired.

Polymers for tissue engineering and/or drug delivery can also be used. Electrically conducting polymers such as polyaniline, polypyrrole, polythiophene, and their derivatives (mainly aniline oligomer and poly(3,4-ethylenedioxythiophene)), or combinations thereof and combinations with other polymers can be used.

Polymers can include α-hydroxycarboxylic acids and copolymers thereof, including PGA, PLA and copolymers thereof, polyethylene oxide/polyethylene terephthalates, copolymers of lactic or glycolic acid, poly(alkylene glycols) of various molecular weights, biodegradable and biocompatible polycaprolactones, polyhydroxybutyrates and copolymers of polyesters, polycarbonates, polyanhydrides and poly(ortho esters), bisphenol-A based polyphosphoesters, including poly(bisphenol-A phenylphosphate), poly(bisphenol-A ethylphosphate), poly(bisphenol-A ethylphosphonate), poly(bisphenol-A phenylphosphonate), poly[bis(2-ethoxy)hydrophosphonic terephthalate], and copolymers of bisphenol-A based poly(phosphoesters), copolymers of polyethylene oxide/polyethylene terephthalate, polymers of tyrosine-derived diphenol compounds, polycarbonates, polyiminocarbonates, polyarylates, polyurethanes, polyethers, and the like.

Some bioinks which can be used with an extrusion function and/or for curing include hydrogels based on RGD-conjugated polysaccharide bioinks with or without fibrin described in U.S. Published Application No. 2019/0160203, modified cellulose nanofibrils with extracellular matrix components described in U.S. Published Application No. 2019/0209738, and nanocellulose bioinks described in U.S. Published Application No. 2017/0368225, each of which is hereby incorporated by reference herein.

Bioinks that can be used include a double-network bioink comprising a non-crosslinkable thickener and a cross-linkable polyethylene glycol-based network that interpenetrate each other. Such bioinks can comprise (a) a biocompatible or non-biocompatible thickener; (b) a polyethylene glycol based crosslinkable network; a photoinitiator; and/or optionally, additives to impart different characteristics; wherein the thickener and polyethylene glycol based crosslinkable network form a structure comprising two interpenetrating networks. In embodiments, the bioink can comprise a thickener chosen from one or more of: polyethylene oxide; polypropylene oxide; nanofibrillar cellulose; nanocrystalline cellulose; gelatin; collagen; glucomannan; alginate; k-carrageenan; bentonite clay; and/or xanthan gum. In embodiments, the cross-linkable polyethylene glycol can comprise one or more reactive groups, including: acrylate; thiol; maleimide; and/or biotin. In embodiments, the polyethylene glycol crosslinker can exhibit structures or blends that are: linear; branched; 4-arm; 8-arm; and/or hyperbranched. In embodiments, the additives can comprise monoacrylate PEG with functionalization of the following: fluorescent groups such as fluorescein, rhodamine, or dansyl; sulfonate groups; amine groups; phosphate groups; lipid groups; and/or CNT binding. In embodiments, the photoinitiator can comprise one or more of Irgacure 2959; LAP; Eosin-Y; and/or Avidin. An exemplary double-network bioink composition according to embodiments of the invention can include (a) one or more thickener present in an amount ranging from 0.1% to 20% w/v of the composition, (b) one or more PEGDA crosslinker present in an amount ranging from 0.1% to 10% w/v of the composition, (c) one or more photoinitiator present in an amount ranging from 0.05% to 1% w/v of the composition, and (d) optionally one or more supplementary proteins present in an amount ranging from 0.01% to 10% w/v of the composition, with the remainder comprising water and salts. By varying the type and/or amount of any one or more of the thickener, PEGDA crosslinker and/or photoinitiator, the mechanical stiffness, the diffusivity, the elasticity, binding capacity, etc. of the construct can be varied. The elasticity and stiffness of the cross-linked bioink can be controlled by changing the blending ratio between the thickener, cross-linking polymer, and the concentration of the photoinitiator.

Bioinks also include biogum-hydrogel bioinks (for example comprising a xanthan gum-based bioink, and one or more biomaterials derived from mammalian, plant, microbial or synthetically derived hydrogels) and/or botanical gum-hydrogel bioinks (for example comprising a botanical gum-based bioink, and one or more biomaterials derived from mammalian, plant, microbial or synthetically derived hydrogels). In embodiments, the bioink compositions can be provided with cells, preferably human cells. In embodiments, the bioink compositions can comprise a ratio of biogum versus biomaterial, or a ratio of botanical gum versus biomaterial, in the interval from 5:95 to 95:5. In embodiments, the biomaterial hydrogel can be at least one of the following constituents for cross-linking purposes and/or to contribute to rheological properties of the bioink, such as hydrocolloids or thickening and gelling agents: collagen type I, collagen and its derivatives, gelatin methacryloyl, gelatin and its derivatives, fibrinogen, thrombin, elastin, alginates, agarose and its derivatives, glycosaminoglycans such as hyaluronic acid and its derivatives, chitosan, low and high methoxy pectin, gellan gum, diutan gum, glucomannan gum, carrageenans, nanofibrillated cellulose, microfibrillated cellulose, crystalline nanocellulose, carboxymethyl cellulose, methyl and hydroxypropylmethyl cellulose, bacterial nanocellulose, or a combination of these constituents. In embodiments, the bioink compositions can configured such that the xanthan-gum bioink has a concentration in the interval from 0.5 to 10% (w/v) or the botanical gums bioink has a concentration in the interval from 0.5 to 50% (w/v). In embodiments, the bioink comprises additional biopolymers for cross-linking purposes and/or to contribute to rheological properties of the bioink, such as hydrocolloids or thickening and gelling agents, for example, alginates, hyaluronic acid and its derivatives, agarose and its derivatives, chitosan, fibrin, gellan gum, silk nanofibrillated cellulose, microfibrillated cellulose, crystalline nanocellulose, bacterial nanocellulose, carrageenans, elastin, collagen and its derivatives as well as gelatin and its derivatives. In embodiments, the concentration of cells, such as human or animal cells, is in the interval from 0.1 million/ml to 150 million/ml. In embodiments, the cells are of human or porcine origin, preferably human origin. In embodiments, the composition is provided in physiological conditions, such as having a pH-value for the composition in the interval from 5-8, preferably 7 and/or an osmolarity of the composition is in the interval from 275 to 300 mOsm/kg, preferably 295 mOsm/kg.

Exemplary bioinks which can be used include, but are not limited to, the following available from CELLINK (Gothenburg, Sweden):

TABLE I

Exemplary Bioinks

| Bioink | Components |
|---|---|
| CELLINK A | Alginate |
| CELLINK A-RGD | Alginate coupled with L-arginine-Glycine-L-aspartic Acid peptide |
| CELLINK Bioink | Alginate & Nanofibrillar cellulose |
| CELLINK BONE | CELLINK & Tricalcium phosphate |
| CELLINK FIBRIN | CELLINK & Fibrinogen |
| CELLINK LAMININK+ | CELLINK & Laminin blend |
| CELLINK LAMININK 111 | CELLINK & Laminin a1b1y1 |
| CELLINK LAMININK 121 | CELLINK & Laminin a1b2y1 |
| CELLINK LAMININK 411 | CELLINK & Laminin a4b1y1 |
| CELLINK LAMININK 521 | CELLINK & Laminin a5b2y1 |
| CELLINK RGD | CELLINK & Alginate coupled with L-arginine-Glycine-L-aspartic Acid peptide |
| CELLINK SKIN | CELLINK & Fibrinogen |
| Coll 1 | Collagen type 1 |
| ColMA | Collagen methacrylate |
| Bio Conductink | Gelatin methacrylate & Carbon nanotubes |
| GelMA | Gelatin methacrylate |
| GelMA A | Gelatin methacrylate & Alginate |
| GelMA C | Gelatin methacrylate, Nanofibrillar cellulose & Alginate |
| GelMA HA | Gelatin methacrylate & Methacrylated hyaluronic acid |
| GelMA HIGH | High-concentration gelatin methacrylate. |
| GelXA | Gelatin methacrylate, Xanthan Gum & Alginate |
| GelXA BONE | Gelatin methacrylate, Xanthan Gum, Alginate, Tricalcium phosphate & Hydroxyapatite |
| GelXA FIBRIN | Gelatin methacrylate, Xanthan Gum, Alginate & Fibrinogen |
| GelXA LAMININK+ | Gelatin methacrylate, Xanthan Gum, Alginate & Laminin blend |
| GelXA LAMININK 111 | Gelatin methacrylate, Xanthan Gum, Alginate & Laminin a1b1y1 |
| GelXA LAMININK 121 | Gelatin methacrylate, Xanthan Gum, Alginate & Laminin a1b2y1 |
| GelXA LAMININK 411 | Gelatin methacrylate, Xanthan Gum, Alginate & Laminin a4b1y1 |
| GelXA LAMININK 521 | Gelatin methacrylate, Xanthan Gum, Alginate & Laminin a5b2y1 |
| GelXA SKIN | Gelatin methacrylate, Xanthan Gum, Alginate & Fibrinogen |
| GelXG | Gelatin methacrylate & Xanthan Gum |
| CELLINK PCL | Polycaprolactone |
| CELLINK PLURONICS | Poloxamer |
| CELLINK START | Polypropylene gel |
| CELLINK START X | CELLINK START. Photo-crosslinkable polymer. |
| CELLINK SUPPORT | Nanofibrillar cellulose |
| CELLINK XPLORE | Cellulose nanocrystals. Alginate. Coloring. |

The monomers (natural or synthetic) can be provided in the bioink resins at an appropriate concentration, such as 0.1% to 20% w/v or higher, such that they react to polymerize upon exposure of the bioink resin to light.

One or more or each bioink resin tank can include one or more photo-initiators within the bioink(s) which can include, for example, free radical photoinitiators, cationic photoinitiators, and anionic photoinitiators. The photoinitiator forms a free radical, cation, or anion which subsequently reacts and catalyzes a polymerization reaction among the monomers within the bioink. Examples of photoinitiators include, but are not limited to benzophenone, benzoin-ether, 2-(dimethylamino)ethanol (DMAE), hydroxyacetophenones, 2-hydroxy-2-methyl-1-phenylpropan-1-one and, hydroxyl-phenyl-ketone, Irgacure® 2959, 2-hydroxy-4'-(2-hydroxyethoxy)-2-methylpropiophenone, (2-hydroxy-1-[4-(2-hydroxyethoxy) phenyl]-2-methyl-1-propanone; lithium phenyl-2,4,6-trimethylbenzoylphosphinate (LAP); (2,2'-azobis[2-methyl-N-(2-hydroxyethyl)propionamide]; 2-isocyanotoethyl methacrylate; benzoyl benzylamine; camphorquinone; thiol-norbornene (thiol-ene); riboflavin; lucirin-TPO; Rose Bengal/furfuryl; ethyl eosin; methacrylic anhydride; 2,2-dimethoxy-2-phenylacetophenone; and Eosin Y.

One or more or each bioink resin tank can include one or more photo-absorbers within the bioink(s) which can include, for example, compounds such as tartrazine, curcumin, anthocyanin, quinoline yellow, as well as gold nanoparticles. The photo-absorber(s) is included in the bioink(s) to limit or control the polymerization reaction.

The photo-initiators and/or photo-absorbers can be free within the bioink solution or can be bound to the one or more monomers, such as through covalent bonding. The photo-initiators and photo-absorbers can be added to the bioink resins at concentration ratios which produce a desired rate of polymerization.

One or more or each bioink resin tank can include one or more types of living cells within the bioink(s) which can be or include, for example, cells from tissues such as liver, kidney, heart, lung, gastrointestinal, muscle, skin, bone, cartilage, vascularized tissues, blood vessels, ducts, ear, nose, esophagus, trachea, and eye. These can include endothelial cells, skin cells such as keratinocytes, melanocytes, Langerhans' cells, and Merkel cells, connective tissue cells such as fibroblasts, mast cells, plasma cells, macrophages, adipocytes, and leukocytes, bone tissue cells such as osteoblasts, osteoclasts, osteocytes, and osteoprogenitor (or osteogenic) cells, cartilage cells such as chondrocytes and chondroblasts, muscle cells such as smooth muscle cells, skeletal muscle cells, cardiac muscle cells, any cells having muscle fibers such as type I (slow twitch), type IIa and type IIb (fast twitch), nerve cells such as multipolar neurons, bipolar neurons, unipolar neurons, sensory neurons, interneurons, motor neurons, neurons of the brain (e.g. Golgi cells, Purkinje cells, pyramidal cells), glial cells such as oligodendrocytes, astrocytes, ependymal cells, Schwann cells, microglia, and satellite cells, liver cells such as hepatocytes, biliary epithelial cells (cholangiocytes), stellate cells, Kupffer cells, and liver sinusoidal endothelial cells, kidney cells such as glomerulus parietal cells, glomerulus podocytes, proximal tubule brush border cells, Loop of Henle thin segment cells, thick ascending limb cells, kidney distal tubule cells, collecting duct principal cells, collecting duct intercalated cells, and interstitial kidney cells, pancreatic cells such as islets cells, alpha cells, beta cells, delta cells, PP cells, endocrine gland cells such as pancreatic cells, hypothalamus cells, pituitary cells, thyroid cells, parathyroid cells, adrenal cells, pineal body cells, and ovarian cells and testicular cells, exocrine gland cells such as sweat gland cells, salivary gland cells, mammary gland cells, ceruminous gland cells, lacrimal gland cells, sebaceous gland cells, and mucous gland cells, epithelial cells such as squamous cells, cuboidal cells, and columnar cells arranged in architectures such as simple, stratified, and pseudostratified, primary cells, immortalized cells, stem cells such mesenchymal stem cells, hematopoietic stem cells, embryonic stem cells, pluripotent stem cells, multipotent stem cells, totipotent stem cells, as well as xenogeneic cells, autologous cells, and allogenic cells, and any combination thereof. The cells can first be grown in suspension or on cell or tissue culture plates as is known in the art, then harvested and added to the bioink resin prior to printing.

One or more or each bioink resin tank can include one or more therapeutic agents or particles within the bioink(s), which can have a molecular weight in the range of less than 900 Daltons for small molecules to up to 1000 kDa for biologics. The concentration of the small molecule or biologic therapeutics can be chosen according to published studies which reveal effective concentrations, such as preclinical or clinical pharmacology data. The small molecules can be any small molecule used in the treatment of any disease, including diseases of the eye, ear, nose, throat, mouth, lung, heart, liver kidney, spleen, pancreas, gastrointestinal system, circulatory system, reproductive system, central nervous system, immune system, musculoskeletal system, and skin. The small molecules can be found or identified in publicly available drug references (see Remington, The Science and Practice of Pharmacy. Easton, Pa.: Mack Pub. Co., 1995; Goodman, L. S., Brunton, L. L., Chabner, B., & Knollmann, B. C. (2011). Goodman & Gilman's pharmacological basis of therapeutics. New York: McGraw-Hill; O'Neil, M. J. (2006). The Merck index: An encyclopedia of chemicals, drugs, and biologicals. Whitehouse Station, N.J.: Merck; United States Pharmacopeia and National Formulary). Rockville, Md.: United States Pharmacopeial Convention; 2016; and Center for Drug Evaluation and Research (U.S.), & Center for Drug Evaluation and Research (U.S.). (1985). Orange book: Approved drug products with therapeutic equivalence evaluations. Rockville, Md.: U.S. Dept. of Health and Human Services, Food and Drug Administration, Center for Drug Evaluation and Research, Office of Pharmaceutical Science, Office of Generic Drugs); these and any edition available at the time of this disclosure are hereby incorporated by reference herein in their entireties.

The one or more therapeutic agents or particles within the bioink(s), can be or include, for example, a biologic such as any bioactive protein or peptide, such as growth factors which include, but are not limited to native or modified PDGF, FGF-2, EGF, epiregulin, TGF-alpha, keratinocyte growth factor, keratinocyte growth factor-2 (KGF-2), granulocyte-macrophage colony-stimulating factor (GM-CSF), TGF-beta, insulin-like growth factor I (IGF-I), insulin-like growth factor II (IGF-II), nerve growth factor (NGF), brain-derived neurotrophic factor (BDNF), and human growth hormone (HGH), cytokines which include but are not limited to IL-1 (IL-1α and -β), IL-2, IL-3, IL-4, IL-5, IL-6, IL-8, IL-9, IL-10, IL-11, IL-12, IL-13, IL-16, IL-18, IFN-α, IFN-β, IFN-γ, TNF-α, and TNF-β, and chemokines which include, but are not limited to, any of four subclasses of chemokines (CCL, CXCL, CX 3 CL, and XCL), including CCL2, CCL3 and CCL5, CXCL1, CXCL2 and CXCL8. The biologics can include any of the above, as well as, for example, an antibody, antibody fragment, antibody-drug conjugate, peptide, peptide-drug conjugate, protein, polypeptide, fusion protein, multivalent binding protein, blood and blood product, nucleic acid, nucleotide, oligonucleotide, antisense oligonucleotide, short interfering RNA (siRNA), micro-interfering RNA (miRNA); small, temporal RNA (stRNA); short, hairpin RNA (shRNA), aptamer, ribozyme, viral vector (e.g. adenovirus, adeno-associated virus (AAV), retrovirus, and lentivirus), and non-viral vector (e.g. plasmid). Non-limiting examples of biologics products include adalimumab (Humira), rituximab (Rituxan), etanercept (Enbrel), trastuzumab (Herceptin), bevacizumab (Avastin), infliximab (Remicade), insulin glargine (Lantus), pegfilgrastim (Neulasta), interferon beta-1a (Avonex), ranibizumab (Lucentis), and epoetin alfa (Epogen). Additional biologics can be found in the U.S. Food and Drug Administration's Purple Book, which is publicly available on the U.S. FDA website and hereby incorporated by reference.

The temperature controlled multi-bioink resin tank system is capable of building complex tissue structures, such as branched or unbranched vascular structures, branched or unbranched pulmonary structures, branched or unbranched duct-like structures, bladder-shaped structures, and layered structures.

The temperature controlled multi-bioink resin tank system is capable of use in combination with other 3D bioprinting technologies, including extrusion, inkjet, acoustic/ultrasound, laser, and stereolithography technologies.

The temperature controlled multi-bioink resin tank system can be used in a clean room to maintain sterile conditions or can be incorporated into clean chamber technology such as described in U.S. Patent Application Publication No. US 20180326665A1, incorporated herein by reference in its entirety.

FIG. 1 is a schematic diagram showing a print surface and the progression of different bioinks photocured on the surface with a side projector according to an embodiment. The print surface (1) is vertically lowered into bioink resin tank one and the first section of the sphere is polymerized through DLP/CAL onto the print surface (2). Upon completion, the print surface is raised and resin tank two moves into position with the print surface. The print surface is lowered into bioink resin tank two and polymerized through DLP/CAL onto the previous bioprinted layer (3). Upon completion, the print surface is raised and resin tank three moves into position with the print surface. The print surface is lowered into bioink resin tank three and polymerized through DLP/CAL on the previous bioprinted layer (4). Upon completion, a three-cell type multi-layered bioprinted spherical structure is created on the print surface.

Figure 2A:
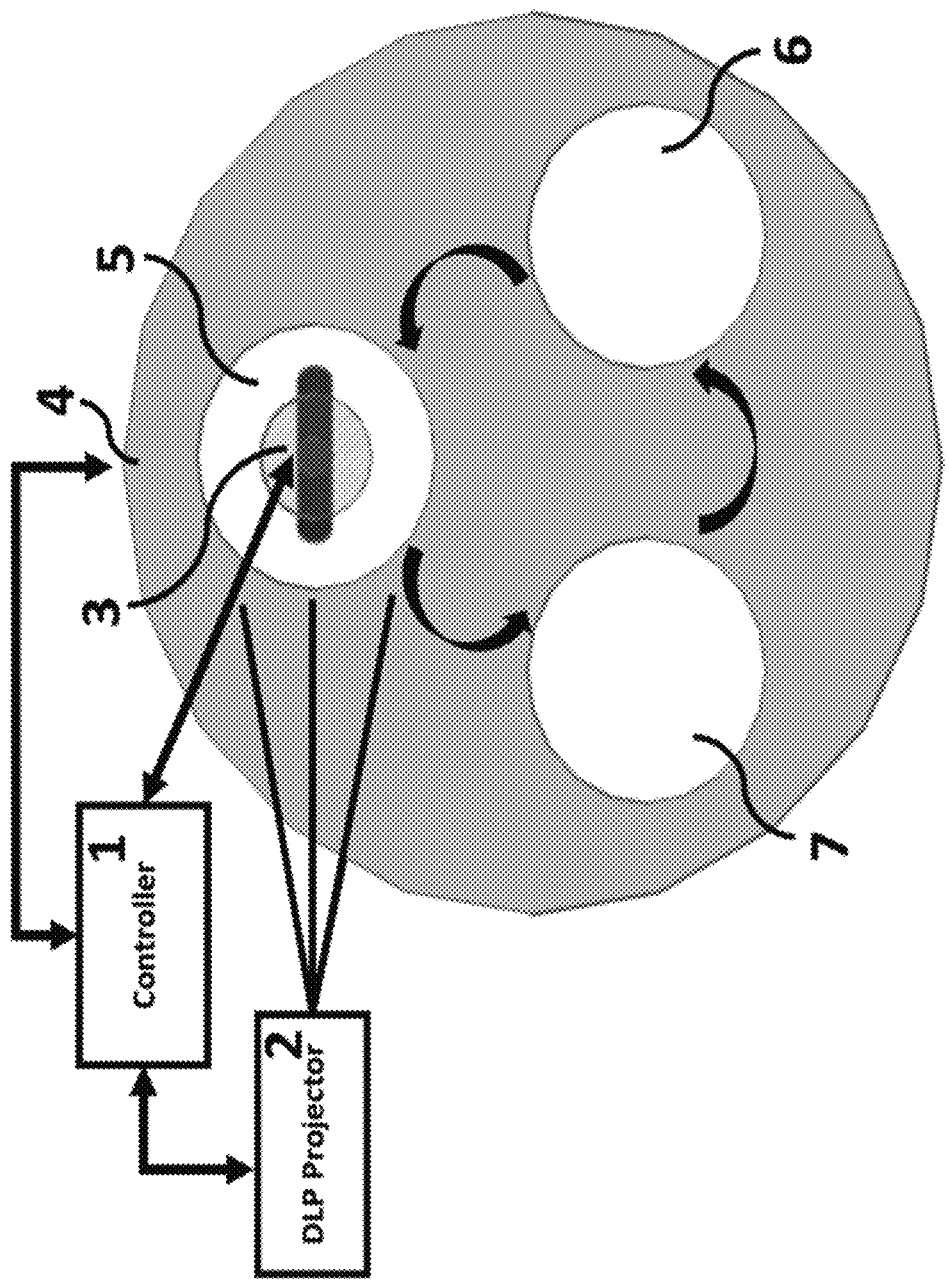
FIG. 2A is a schematic diagram showing a top view of an embodiment of a multi-bioink resin tank system for 3D bio-overprinting.

FIG. 2A is a schematic diagram showing a top view of an embodiment of a multi-bioink resin tank system for 3D bio-overprinting which includes a controller (1) that commands and DLP/CAL projector (2), vertical motion of a print surface (3), and horizontal rotation of a temperature-controlled platform or stage (4) with multiple temperature-controlled bioink resin tanks (5,6,7). One or more or each bioink resin tank can move into position with the DLP projector and under the print surface consecutively to form a multi-layered tissue on the inflated surface. Movement of one or more components of the system can be relative to one or more other component(s) of the system. For example, one or more light source can move and/or one or more print surface can move, and/or one or more bioink tank can move, and/or one or more platform on which one or more bioink tank is positioned can move.

Figure 2B:
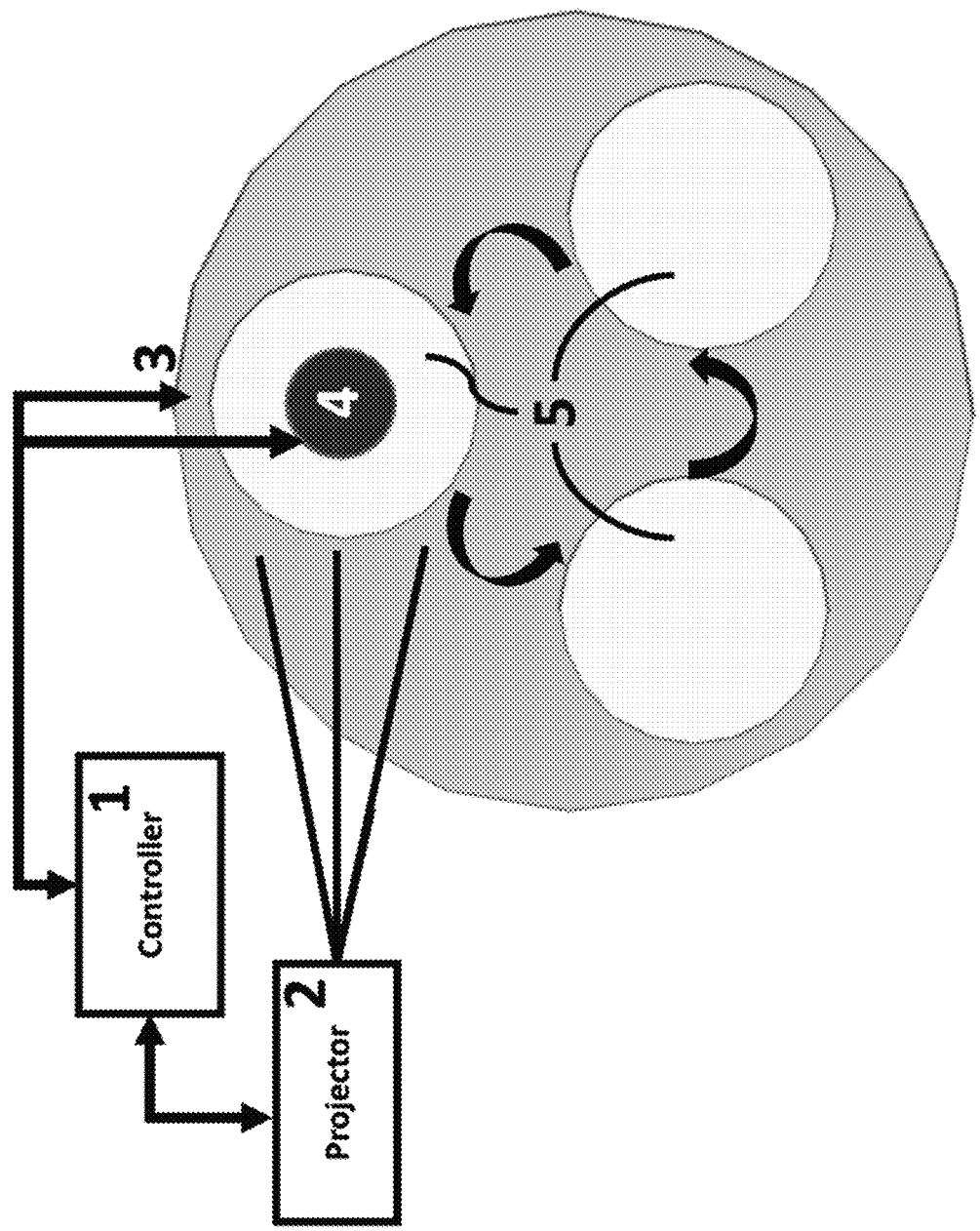
FIG. 2B is a schematic diagram showing a top view of another embodiment of a multi-bioink resin tank system for 3D bio-overprinting.

FIG. 2B is a schematic diagram showing a top view of an embodiment of a multi-bioink resin tank system for 3D bio-overprinting which includes a controller (1) which commands multiple functions of the system. The controller commands the side projector (2), the horizontal rotation of the temperature-controlled platform or stage (3), the vertical and circular motion of the print surface (4), and the multiple temperature-controlled bioink resin tanks with circular motion (5). One or more or each bioink resin tank moves into position with the projector and under the print surface consecutively to form a multi-layered tissue on the surface.

Figure 3A:
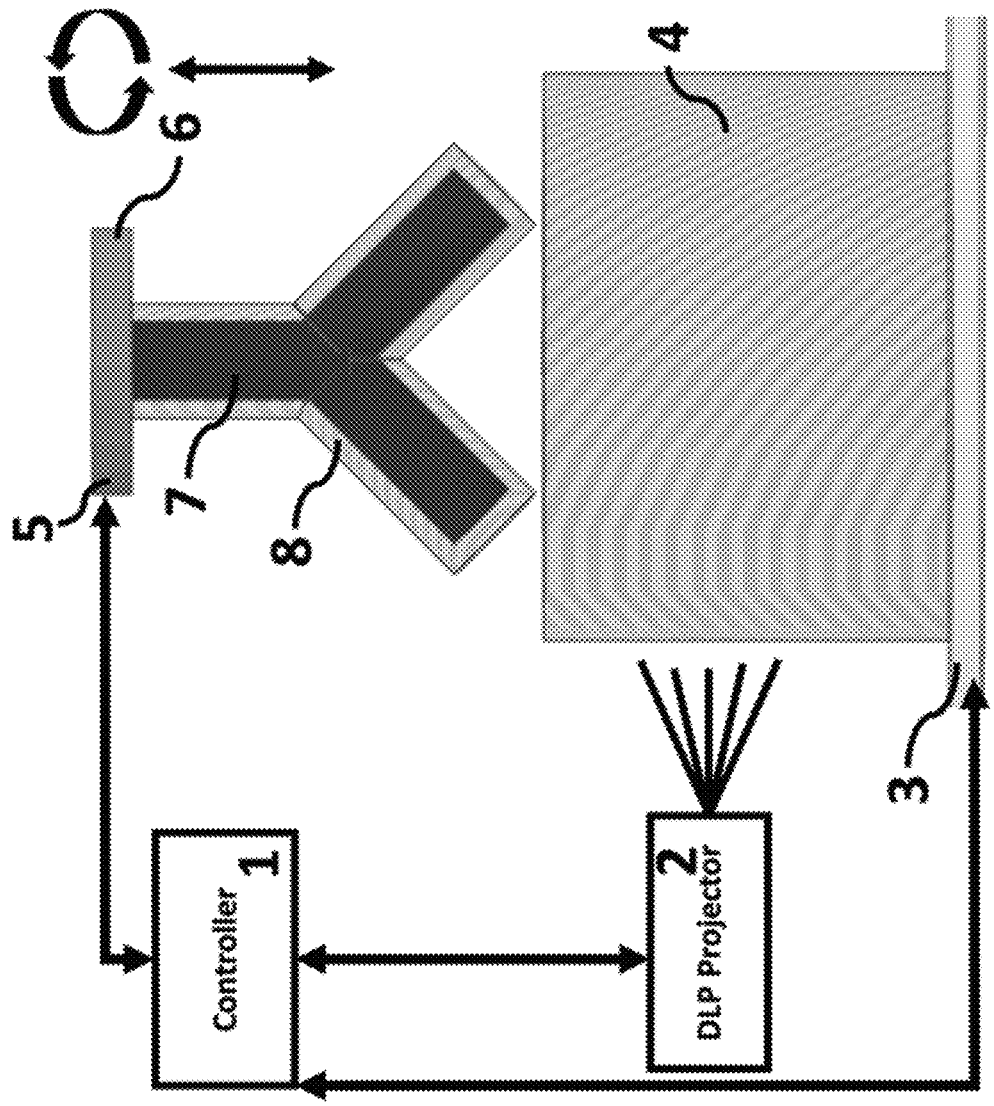
FIG. 3A is a schematic diagram showing a side view of an embodiment of a multi-bioink resin tank system for 3D bio-overprinting with one projector.

FIG. 3A is a schematic diagram showing a side view of an embodiment of a multi-bioink resin tank system for 3D bio-overprinting with one projector. The system includes a controller (1) that commands a DLP projector (2), the horizontal rotation of a temperature-controlled platform or stage (3) with multiple temperature-controlled bioink resin tanks (4), and the print surface (5,6,7) with vertical and circular rotational motion and an inflatable feature (7). The controller and the system allow for multi-layer multi-material bioprinting on the inflatable print surface (8).

Figure 3B:
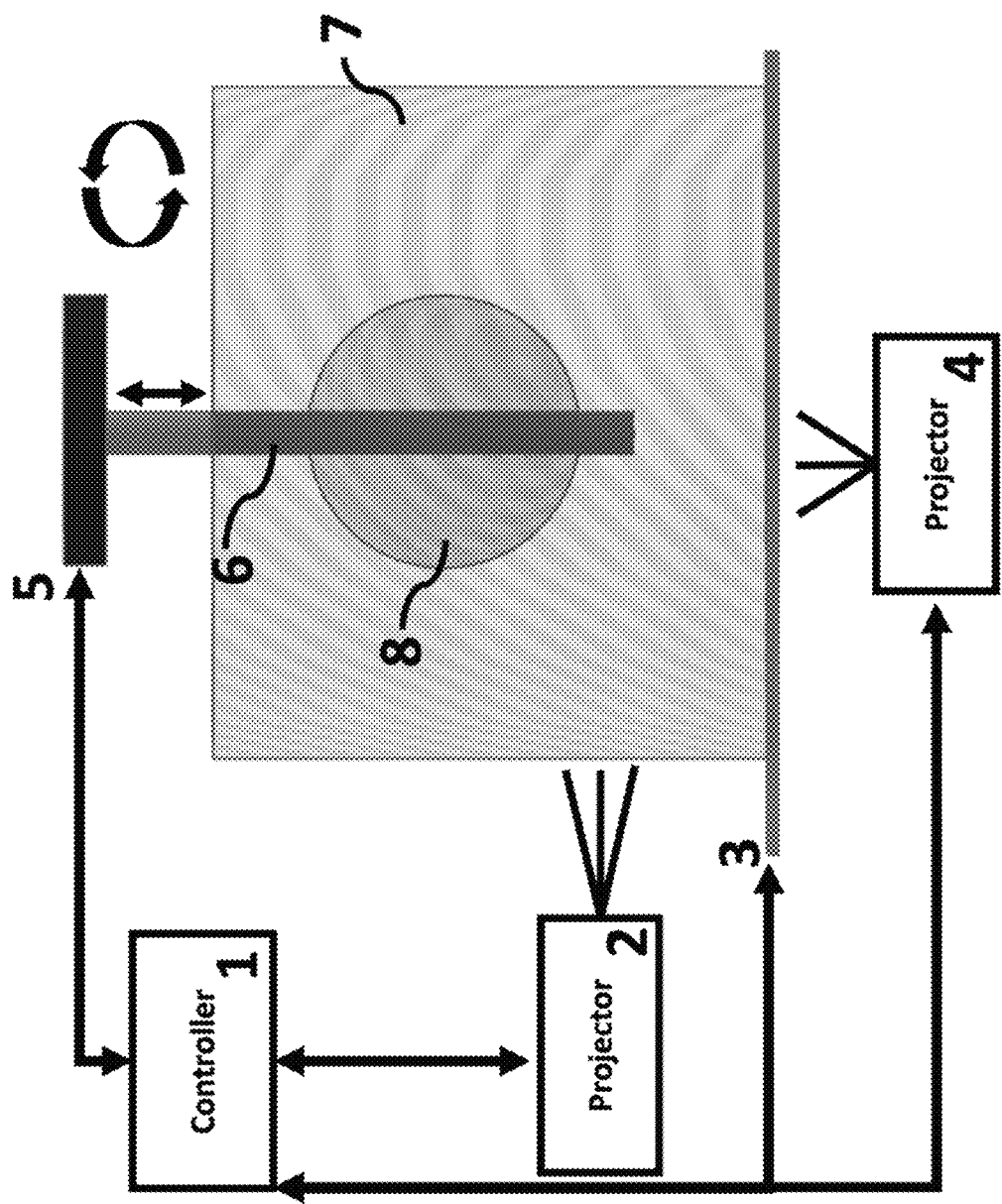
FIG. 3B is a schematic diagram showing a side view of an embodiment of a multi-bioink resin tank system for 3D bio-overprinting with two projectors.

FIG. 3B is a schematic diagram showing a side view of an embodiment of a multi-bioink resin tank system for 3D bio-overprinting with two projectors. The controller (1) commands multiple functions of the system. The controller commands the side projector (2), the horizontal rotation of the temperature-controlled platform or stage (3), the bottom projector (4), the vertical and circular motion of the print surface (5,6), and the temperature-controlled bioink resin tanks with circular motion (7). The system allows for photo-polymerization of a bioinks on the print surface (8).

Figure 4:
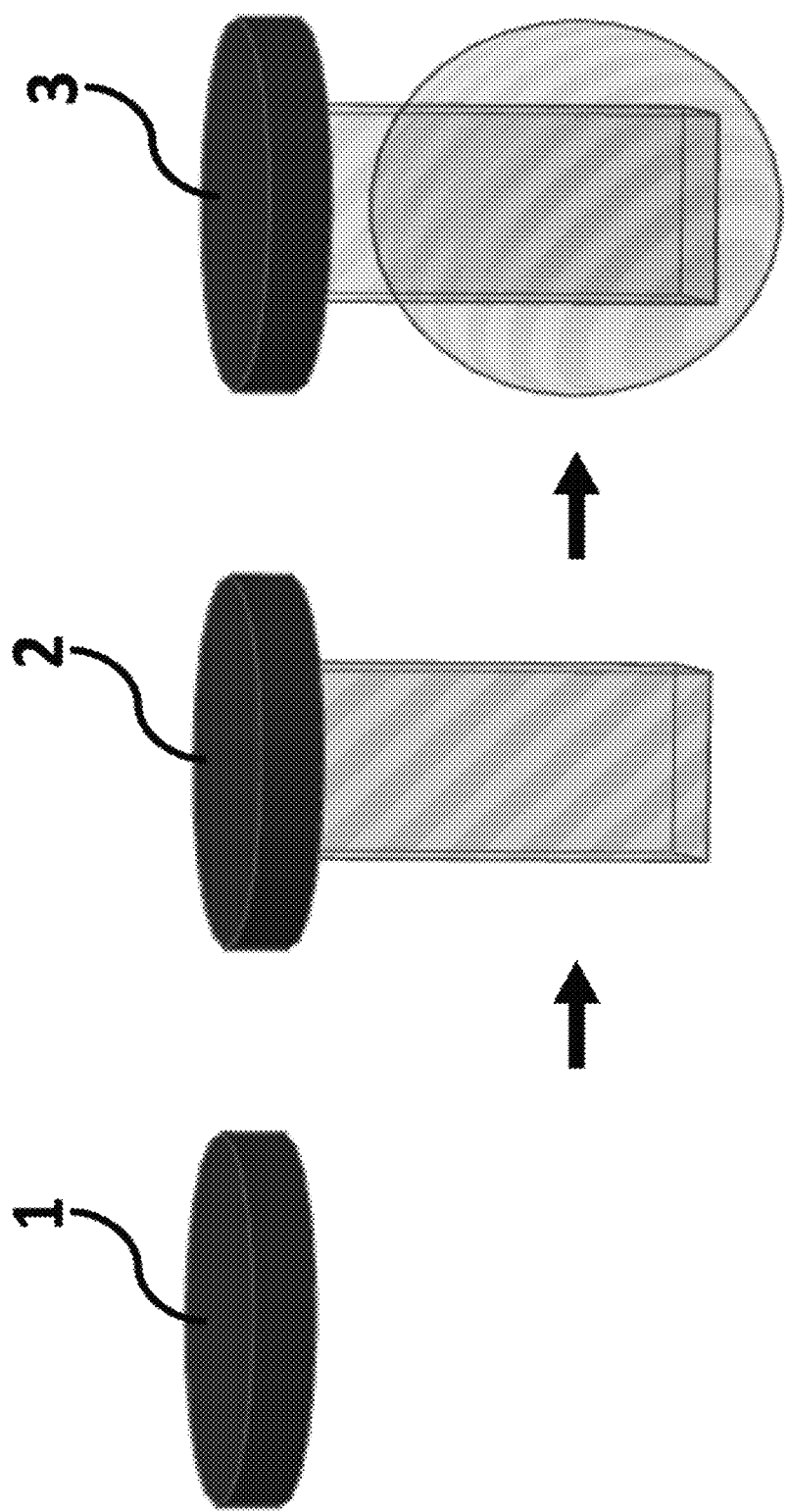
FIG. 4 is a schematic diagram showing multi-projector printing and the progression of different bioinks photocured on the printing surface according to an embodiment.

FIG. 4 is a schematic diagram showing multi-projector printing and the progression of different bioinks photocured on the surface. The print surface (1) is vertically lowered into bioink resin tank one and the first section is polymerized with the bottom projector onto the print surface (2). Upon completion, the print surface is raised and resin tank two moves into position with the print surface. The print surface is lowered into bioink resin tank two and polymerized with the side projector onto the previous bioprinted layer (3).

Figure 5:
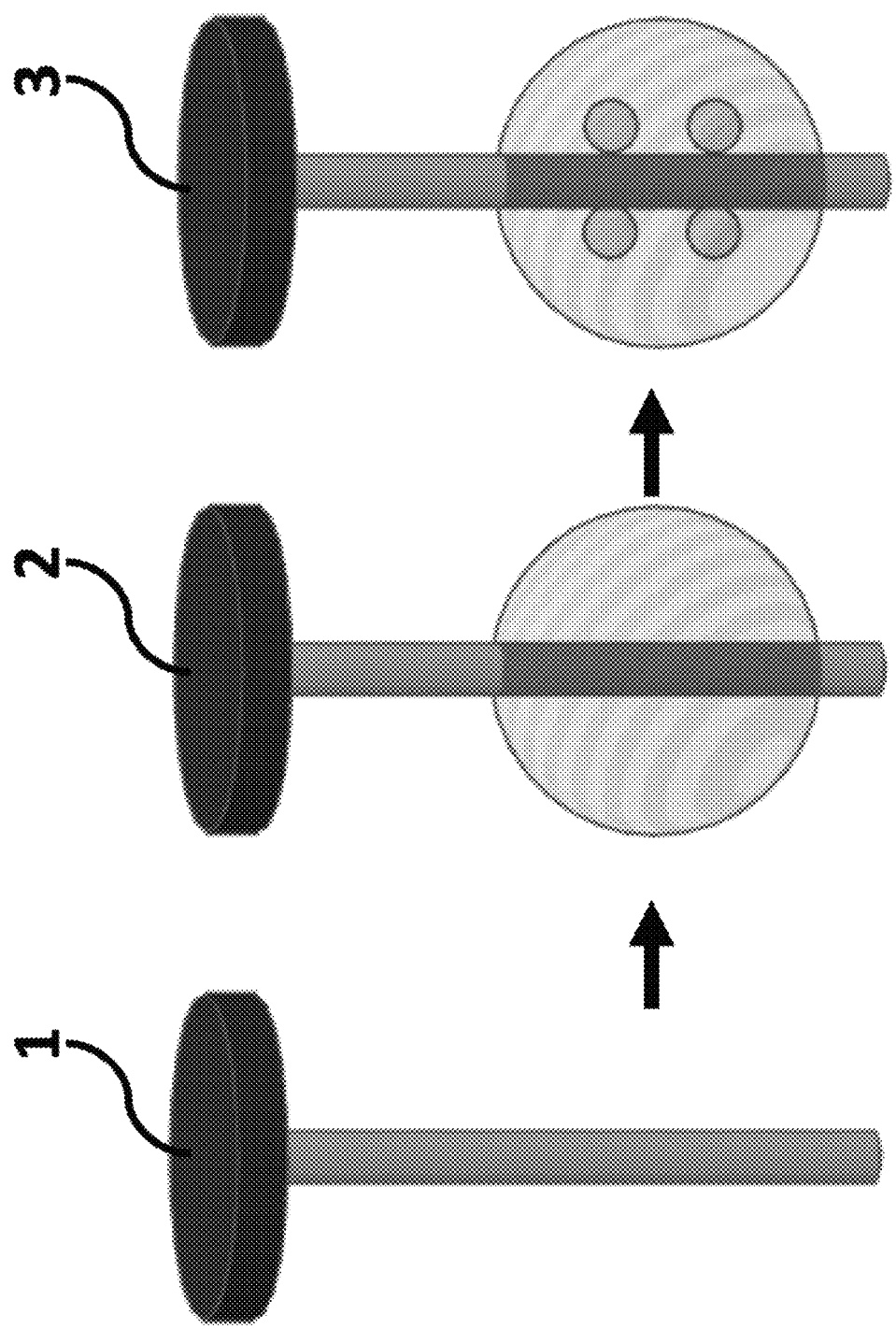
FIG. 5 is a schematic diagram of a print surface with an extrusion function according to an embodiment.

FIG. 5 is a schematic diagram of a print surface with an extrusion function. The print surface (1) is vertically lowered into a bioink resin tank and a sphere is polymerized through DLP/CAL onto the print surface (2). Upon completion, the print surface extrusion function is initiated and a bioink is extruded out of the print surface and into the polymerized sphere at specific points. In embodiments, one or more materials can be dispensed by way of a sprayer, or other device for dispensing materials without direct contact with the printed structures and/or the print surface. For example, an air-brush type sprayer can be used that can spray additional cells, drugs, nanofibers, etc. between layers or around the printed structures.

Example 1

A 3D file is created containing a model of a hollow Y-branched vascular tube (50×50×10 mm) with three layered sections. Each of the three sections are 2 mm in width and represent a different bioink that will be consecutively photopolymerized on the print surface that mimics the model. The mimicking surface is a rubber polymer that is inflated and vertically lowered into the temperature-controlled multi-bioink resin tanks and rotates in a circular motion. The bioprinting software controller recognizes each model section and makes adjustments to each tank position, the print surface, and the projector based on the model coordinates and bioprinting progress. Three individual bioink resin tanks are each set and maintained at 4 degrees C. during the bioprinting. Bioink resin tank one is loaded with a photopolymerizable collagen solution, a photo-initiator, a photo-absorber, and human smooth muscle cells. Bioink resin tank two is loaded with a photopolymerizable collagen solution, a photo-initiator, a photo-absorber, and human fibroblast cells. Bioink resin tank three is loaded with a photopolymerizable collagen solution, a photo-initiator, a photo-absorber, and human endothelial cells. The print surface is inflated and is vertically lowered into bioink resin tank one and polymerized through DLP/CAL onto the print surface until 2 mm thickness is achieved. Upon completion, the print surface is raised and resin tank two moves into position with the print surface. The print surface is lowered into bioink resin tank two and polymerized through DLP/CAL onto the previous bioprinted layer until 2 mm thickness is achieved. Upon completion, the print surface is raised and resin tank three moves into position with the print surface. The print surface is lowered into bioink resin tank three and polymerized through DLP/CAL on the previous bioprinted layer until 2 mm thickness is achieved. Upon completion, a three-cell type multi-layered bioprinted construct is engineered on the print surface. After printing is complete the print surface is deflated and the bioprinted multi-layered structure is rinsed and incubated with cell culture media.

Example 2

Same as Example 1, but after printing is complete the print surface with the bioprinted multi-layered structure is rinsed and placed into cell culture media. The inflate and deflate function of the system is used as a mechanical force bioreactor on the bioprinted multi-layered structure.

Example 3

A 3D file is created containing a model of a sphere (50×50×10 mm) with three layered sections. Each of the three sections represents a different bioink that will be consecutively photopolymerized on the print surface. The print surface and bioink tank both rotate in a circular motion during the photo-curing which is achieved by the side projector. The bioprinting software controller recognizes each model section and makes adjustments to the print surface, the bioink tank positions, and the side projector based on the model coordinates and bioprinting progress.

The three individual bioink resin tanks are each set and maintained at 4 degrees C. during the bioprinting. Bioink resin tank one is loaded with a photopolymerizable collagen solution, a photo-initiator, a photo-absorber, and human smooth muscle cells. Bioink resin tank two is loaded with a photopolymerizable collagen solution, a photo-initiator, a photo-absorber, and human fibroblast cells. Bioink resin tank three is loaded with a photopolymerizable collagen solution, a photo-initiator, a photo-absorber, and human endothelial cells. The print surface is vertically lowered into bioink resin tank one and the first section of the sphere is polymerized through DLP/CAL onto the print surface. Upon completion, the print surface is raised and resin tank two moves into position with the print surface. The print surface is lowered into bioink resin tank two and polymerized through DLP/CAL onto the previous bioprinted layer. Upon completion, the print surface is raised and resin tank three moves into position with the print surface. The print surface is lowered into bioink resin tank three and polymerized through DLP/CAL on the previous bioprinted layer. Upon completion, a three-cell type multi-layered bioprinted spherical structure is engineered on the print surface (FIG. 1). After printing is complete the bioprinted multi-layered sphere is rinsed and incubated with cell culture media.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. A method of three-dimensional (3D) bioprinting, comprising:
   disposing a printing surface, or portion thereof, into a container comprising a first bioink resin, wherein the printing surface or portion thereof is positioned at a selected distance from one or more DLP projectors;
   rotating the printing surface or portion thereof and curing two or more layers on the printing surface or portion thereof, each layer comprising one or more bioink resin;
   wherein the curing is performed with the one or more digital light processing (DLP) projectors positioned in a manner such that electromagnetic energy is emitted from the one or more DLP projectors in a direction parallel to a bottom surface of the container and such that the electromagnetic energy enters the container in a direction parallel to the bottom surface of the container;
   wherein the curing is performed with the printing surface or portion thereof positioned at the same selected distance from the one or more DLP projectors, which is a distance measured in a plane parallel to the bottom surface of the container; and
   removing the printing surface, or portion thereof, from the container;
   thereby preparing a 3D bioprinted structure.

2. The method of claim 1, further comprising:
   disposing the printing surface, or portion thereof, into a subsequent substance;
   optionally curing one or more layers comprising the subsequent substance;
   removing the printing surface, or portion thereof, from the subsequent substance;
   and optionally repeating the disposing, curing and removing with one or more additional substances to produce one or more layers comprising the additional substance.

3. The method of claim 2, wherein:
   the disposing is performed by mechanically positioning the printing surface, or portion thereof, into the container;
   the curing is performed by irradiating the printing surface, or portion thereof, with the electromagnetic energy; and the removing is performed by mechanically positing the printing surface, or portion thereof, out of the container.

4. The method of claim 3, wherein the disposing is performed by way of one or more actuators capable of rotary and vertical motion.

5. The method of claim 3, further comprising consecutively positioning the first bioink resin and the subsequent and/or additional substance(s) below the printing surface, or portion thereof.

6. The method of claim 5, wherein the container containing the first bioink resin is mechanically re-positioned and a subsequent container containing the subsequent and/or additional substance is disposed below the printing surface, or portion thereof.

7. The method of claim 3, wherein the irradiating is performed with ultraviolet, visible, or infrared light from the one or more digital light processing (DLP) projectors.

8. The method of claim 3, wherein the curing of the first bioink resin, the subsequent substance and/or the additional substance comprises photopolymerization to form one or more polymers initiated by one or more photo-initiators and controlled by one or more photo-absorbers.

9. The method of claim 3, wherein the first bioink resin, the subsequent substance and/or the additional substance comprises one or more living cells and/or therapeutic agents.

10. The method of claim 1, wherein the printing surface, or portion thereof, is inflatable.

11. The method of claim 3, further comprising controlling temperature during the disposing, curing, and/or removing by way of one or more temperature control units.

12. The method of claim 3, further comprising extruding or spraying one or more materials chosen from cells, drugs, nanofibers, and/or therapeutic agents between and/or on one or more of the layers comprising the first bioink resin, the subsequent substance and/or the additional substance.

13. The method of claim 1, wherein the curing is performed with a first digital light processing projector and a second digital light processing projector, the first and second digital light processing projectors positioned in a manner such that electromagnetic energy is emitted:
    from the first digital light processing projector into the container in a direction parallel to the bottom surface of the container; and
    from the second digital light processing projector into the container in a direction perpendicular to the bottom surface of the container.

14. The method of claim 1, wherein during the curing the one or more DLP projectors remain stationary.

15. A method of three-dimensional (3D) bioprinting, comprising:
    disposing a printing surface, or portion thereof, into a container comprising a first bioink resin, wherein the disposing into the container is performed along a z-axis and the printing surface or portion thereof is positioned on the z-axis at a selected distance x measured from one or more DLP projectors in an x-y plane perpendicular to the z-axis;
    rotating the printing surface or portion thereof along the z-axis and curing two or more layers on the printing surface or portion thereof, each layer comprising one or more bioink resin,
        wherein the curing is performed with the one or more digital light processing (DLP) projectors positioned in a manner such that electromagnetic energy is emitted from the one or more DLP projectors in a direction parallel to a bottom surface of the container and such that the electromagnetic energy enters the container in a direction parallel to the bottom surface of the container,
        wherein the curing is performed with the printing surface or portion thereof positioned at the same selected distance x measured from the one or more DLP projectors; and
    removing the printing surface, or portion thereof, from the container;
    thereby preparing a 3D bioprinted structure.

* * * * *